(12) United States Patent
Kathirgamanathan et al.

(10) Patent No.: US 8,507,896 B2
(45) Date of Patent: Aug. 13, 2013

(54) COMPOUNDS HAVING ELECTROLUMINESCENT OR ELECTRON TRANSPORT PROPERTIES

(75) Inventors: Poopathy Kathirgamanathan, Middlesex (GB); Sivagnanasundram Surendrakumar, Middlesex (GB)

(73) Assignee: Merck Patent GmbH, Darmstadt (DE)

( * ) Notice: Subject to any disclaimer, the term of this patent is extended or adjusted under 35 U.S.C. 154(b) by 332 days.

(21) Appl. No.: 12/922,291

(22) PCT Filed: Feb. 24, 2009

(86) PCT No.: PCT/GB2009/050180
§ 371 (c)(1),
(2), (4) Date: Sep. 13, 2010

(87) PCT Pub. No.: WO2009/112854
PCT Pub. Date: Sep. 17, 2009

(65) Prior Publication Data
US 2011/0006295 A1    Jan. 13, 2011

(30) Foreign Application Priority Data
Mar. 11, 2008    (GB) .................................. 0804469.5

(51) Int. Cl.
H01L 35/24    (2006.01)
(52) U.S. Cl.
USPC .................................... 257/40; 257/E51.001
(58) Field of Classification Search
USPC ........................................... 257/40, E51.001
See application file for complete search history.

(56) References Cited

U.S. PATENT DOCUMENTS

| | | |
|---|---|---|
| 4,356,429 A | 10/1982 | Tang |
| 4,720,432 A | 1/1988 | VanSlyke et al. |
| 4,769,292 A | 9/1988 | Tang et al. |
| 5,141,671 A | 8/1992 | Bryan et al. |
| 6,208,075 B1 | 3/2001 | Hung et al. |
| 6,392,250 B1 | 5/2002 | Aziz et al. |

(Continued)

FOREIGN PATENT DOCUMENTS

| | | |
|---|---|---|
| EP | 0373582 A1 | 6/1990 |
| EP | 0891121 A1 | 1/1999 |

(Continued)

OTHER PUBLICATIONS

Hsu, Ming-Ann et al., "Light emitting materials and devices of PPV type compounds containing quinolines", Database CA, Accession No. 2005:1326926 abstract; 2005, XP002525839.

(Continued)

*Primary Examiner* — Anthony Ho
(74) *Attorney, Agent, or Firm* — Novak Druce Connolly Bove + Quigg LLP

(57) ABSTRACT

A compound of the formula $R^1(CR^3\!=\!CR^4)nAr(CR^4\!=\!CR^3)_n R^2$ wherein: n is 0 or 1; Ar represents aryl or heteroaryl having 1-5 aromatic rings which may be chain or fused or a combination of chain and fused, which may be substituted with alkoxy, fluoro, fluoroalkyl or cyano and which in the case of a 5-membered ring nitrogen heteroatom may be N-substituted with aryl or substituted aryl optionally further substituted with alkoxy, fluoro, fluoroalkyl or cyano; $R^1$ and $R^2$ independently represent aryl or nitrogen, oxygen or sulphur-containing heteroaryl having two to four fused aromatic rings one of which may be 5-membered and optionally substituted by aryl or heteroaryl having 1-5 chain or fused aromatic rings which may be further substituted with alkoxy, fluoro, fluoroalkyl or cyano; and $R^3$ and $R^4$ independently represent hydrogen, methyl, ethyl or benzyl.

16 Claims, 1 Drawing Sheet

(56) References Cited

U.S. PATENT DOCUMENTS

| | | |
|---|---|---|
| 6,436,559 B1 | 8/2002 | Ueno et al. |
| 6,720,573 B2 | 4/2004 | Son et al. |
| 7,045,952 B2 | 5/2006 | Lu |
| 7,175,922 B2 | 2/2007 | Jarikov et al. |
| 2002/0074935 A1 | 6/2002 | Kwong et al. |
| 2003/0012980 A1 | 1/2003 | Mouri et al. |
| 2003/0141809 A1 | 7/2003 | Furugori et al. |
| 2004/0155238 A1 | 8/2004 | Thompson et al. |
| 2005/0187375 A1 | 8/2005 | Epstein et al. |
| 2006/0003089 A1 | 1/2006 | Kathirgamanathan |

FOREIGN PATENT DOCUMENTS

| | | |
|---|---|---|
| EP | 1029909 A1 | 8/2000 |
| EP | 1496041 A1 | 1/2005 |
| EP | 1894923 A1 | 3/2008 |
| JP | 09-328472 A | 12/1997 |
| WO | WO-00/32717 A1 | 6/2000 |
| WO | WO-03/006573 A1 | 1/2003 |
| WO | WO-2004/050793 A1 | 6/2004 |
| WO | WO-2004/058783 A1 | 7/2004 |
| WO | WO-2004/058913 A1 | 7/2004 |
| WO | WO-2004/062324 A1 | 7/2004 |
| WO | WO-2004/084325 A1 | 9/2004 |
| WO | WO-2005/080526 A2 | 9/2005 |
| WO | WO-2006/016193 A1 | 2/2006 |
| WO | WO-2006/024878 A1 | 3/2006 |
| WO | WO-2006/040593 A1 | 4/2006 |
| WO | WO-2006/061594 A2 | 6/2006 |
| WO | WO-2006/076092 A1 | 7/2006 |
| WO | WO-2006/090098 A1 | 8/2006 |
| WO | WO-2008/078115 A1 | 7/2008 |
| WO | WO-2008/081178 A1 | 7/2008 |
| WO | WO-2008/120839 A1 | 10/2008 |

OTHER PUBLICATIONS

Fayed, T.A., et al., "Photochemical and laser activity of 1,4-bis [β-(2-quinoxalyl)vinyl]benzene: a new laser dye," Journal of Photochemistry and Photobiology A: Chemistry, 1999, vol. 121, pp. 183-190.

Doi, H., et al.," 2,3,4-triphenyl: quinoline derives. used in organic electroluminescence device—in light emitting layer between anode and cathode", Database WPI, Accession No. 1998-105111, Dec. 22, 1997, XP002525840. (see JP-09-328472-A).

COMPOUNDS HAVING ELECTROLUMINESCENT OR ELECTRON TRANSPORT PROPERTIES

CROSS-REFERENCE TO RELATED APPLICATIONS

This application is a national stage application (under 35 U.S.C. §371) of PCT/GB2009/050180, filed Feb. 24, 2009, which claims benefit of United Kingdom application 0804469.5, filed Mar. 11, 2008.

FIELD OF THE INVENTION

This invention relates to novel compounds, to methods for their preparation and to their use in inter alia optical light emitting devices e.g. as a host in an electroluminescent layer or in an electron transport layer or as an electron transport or other layer in electro-optical devices e.g. photoconductive members such as plates or drums.

BACKGROUND TO THE INVENTION

Kulkarni et al., *Chem. Mater.* 2004, 16, 4556-4573 (the contents of which are incorporated herein by reference) have reviewed the literature concerning electron transport materials (ETMs) used to enhance the performance of organic light-emitting diodes (OLEDs). In addition to a large number of organic materials, they discuss metal chelates including aluminium quinolate, which they explain remains the most widely studied metal chelate owing to its superior properties such as high EA (~−3.0 eV; measured by the present applicants as −2.9 eV) and IP (~−5.95 eV; measured by the present applicants as about −5.7 eV), good thermal stability (Tg ~172° C.) and ready deposition of pinhole-free thin films by vacuum evaporation. Aluminium quinolate remains a preferred material both for use as a host to be doped with various fluorescent materials to provide an electroluminescent layer and for use as an electron transport layer.

SUMMARY OF THE INVENTION

A problem with which invention is concerned is to provide OLEDs of improved performance. A further problem with which the invention is concerned is to provide further materials for use in the electroluminescent and/or or electron transport layer of an OLED or in an electron transport layer of another device e.g. a photoconductive member.

In one embodiment the invention provides a compound of the formula $$R^1(CR^3=CR^4)_nAr(CR^4=CR^3)_nR^2$$

wherein: n is 0 or 1; Ar represents aryl or heteroaryl having 1-5 aromatic rings which may be chain or fused or a combination of chain and fused, which may be substituted with alkoxy, fluoro, fluoroalkyl or cyano and which in the case of a 5-memnered ring nitrogen heteroatom may be N-substituted with aryl or substituted aryl optionally further substituted with alkoxy, fluoro, fluoroalkyl or cyano; $R^1$ and $R^2$ independently represent aryl or nitrogen, oxygen or sulphur-containing heteroaryl having two to four fused aromatic rings one of which may be 5-membered and optionally substituted by aryl or heteroaryl having 1-5 chain or fused aromatic rings which may be further substituted with alkoxy, fluoro, fluoroalkyl or cyano; and $R^3$ and $R^4$ independently represent hydrogen, methyl, ethyl or benzyl.

In embodiments n is 1, and $R^1$ and $R^2$ independently represent bicyclic or tricyclic heteroaryl containing 1-3 ring nitrogen atoms and optionally substituted with any of the substituents defined above. In some embodiments $R^1$ and $R^2$ represent fused bicylcic or tricyclic ring structures having a 5-membered ring. In other embodiments the rings are all 6-membered e.g. $R^1$ and $R^2$ represent quinolinyl. In further embodiments $R^1$ and $R^2$ independently represent imidazole, oxazole or thiazole which in the case of imidazole may be substituted on nitrogen by aryl or heteroaryl e.g. phenyl or substituted phenyl. In some embodiments (but see below with reference to dialdehydes) Ar represents phenyl or naphthyl optionally substituted with fluoro, fluoroalkyl or cyano.

A group of compounds within the above genus is of formula:

wherein n, $R^1$, $R^2$ and Ar are as defined above.

A more specific group of compounds is of formula

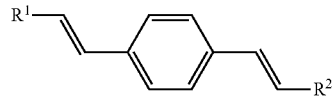

wherein $R^1$ and $R^2$ are as defined above.

In an embodiment $R^1$ and $R^2$ are different e.g. they may be similar ring structures in which one of the rings has a bulky substituent e.g. t-butyl and the other does not.

In embodiments, the new compounds described above may be used as electron transport materials in OLEDs, as electroluminescent materials or as host materials in the electroluminescent layer which may contain an additional host material, being dopable as described below.

In further embodiments the compounds described above may be p-doped or when used to provide an electron transport layer may be n-doped e.g. with lithium, potassium, caesium or another low work function metal. They may be used alone or in admixture with another organic small molecule electron transport material either un-doped or n-doped. They may be used with inorganic electron injection layers e.g. LiF or with organic small molecule electron injection layers e.g. as described below.

Embodiments of the compounds set out above, when incorporated into OLED devices, have exhibited electron mobility greater than that of aluminium quinolate and comparable to or greater than zirconium quinolate and device lifetimes comparable to or greater than that of devices using aluminium quinolate or zirconium quino late.

Also provided is a method of making a compound having electroluminescent and/or electroconductive properties, which comprises condensing an aromatic dialdehyde or diketone with a methyl-, ethyl-, propyl- or benzyl-substituted heteroaryl compound having two to four fused rings which may be unsubstituted or may be further substituted by aryl or heteroaryl having from one to five aromatic rings, said aryl or heteroaryl substituent or substituents optionally being substituted with one or more halo or cyano substituents.

Benzene-1,4-dicarboxaldehyde is preferred. Other dialdehydes that may be employed include any of benzene-1,2-dicarboxaldehyde, benzene-1,3-dicarboxaldehyde, naphthalene 1,2-dicarbaldehyde, naphthalene-1,4-dicarbaldehyde, naphthalene 2,6-dicarbaldehyde, naphthalene-1,8-dicarbaldehyde, anthracene-1,4-dicarbaldehyde, anthracene-2,3-dicarbaldehyde, anthracene-4,9-dicarbaldehyde, anthracene-9, 10-dicarbaldehyde and 2,2'-bipyridine-4,4'- dicarboxaldehyde and biphenyl-4,4'-dicarboxaldehyde. The condensation may be carried out under reflux in the presence of an acid e.g. an anhydride of an organic acid e.g. acetic anhydride which may be employed under reflux.

Representative heteroaromatic dialdehydes include 2,4-pyridine dicarboxaldehyde, 9-benzylcarbazole-3,6-dicarboxaldehyde and 2,2'-bipyridine-4,4'-dicarboxaldehyde.

The invention also provides a composition comprising a compound as aforesaid, optionally a second host or electron transport material, and a dopant.

The invention yet further provides an optical light emitting diode device having a first electrode, a second electrode and a layer comprising a compound as set out above or a composition as set out above between the first and second electrodes.

In embodiments the compound as set out above is comprised in an electron transport layer. In other embodiments the invention may further provide an electroluminescent device having first and second electrodes and between said electrodes an electroluminescent layer which comprises a compound as above which may be doped with a fluorescent dopant, a phosphorescent dopant or an ion fluorescent dopant.

The invention yet further provides an imaging member for creation of an electrostatic latent image containing a compound or composition as set out above.

Other features of the invention are defined in the accompanying claims to which attention is directed.

DESCRIPTION OF PREFERRED FEATURES

Cell structure

Figure 1:
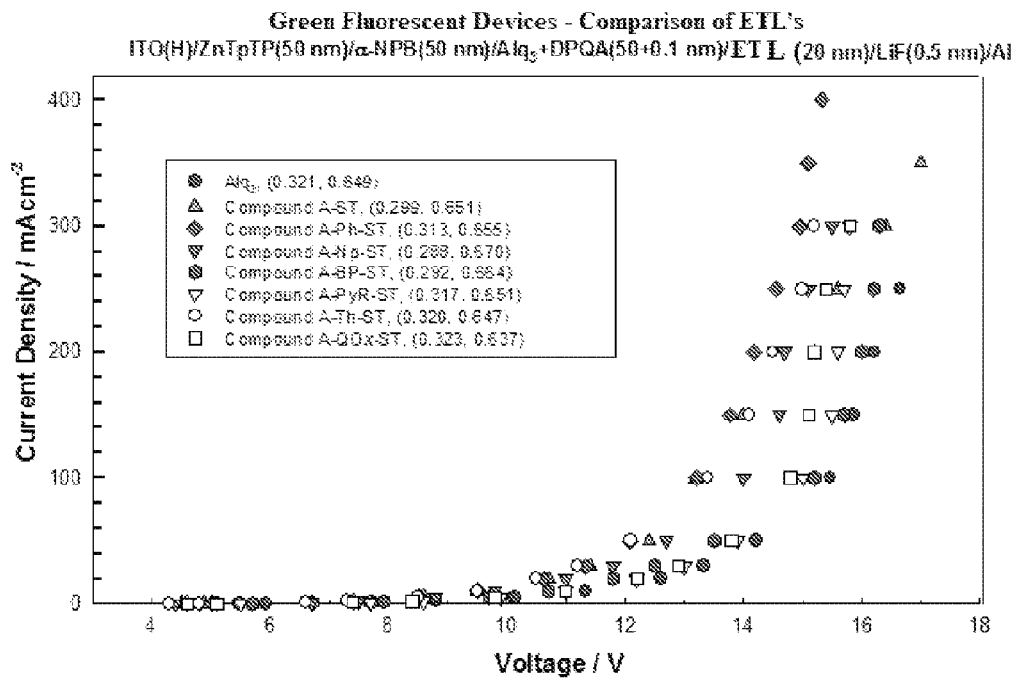
FIGS. 1 and 2 show the CIE colour coordinates and the current density-voltage characteristics.

The OLEDs of the invention are useful inter alia in flat panel displays and typically comprise an anode and a cathode between which is sandwiched a multiplicity of thin layers including an electroluminescent layer, electron injection and/or transport layer(s), hole injection and/or transport layer(s) and optionally ancillary layers. The layers are typically built up by successive vacuum vapour deposition operations, although it may be convenient to form one or more of the layers e.g. the hole injection and hole transport layers by other methods e.g. spin coating or ink jet printing.

A typical device comprises a transparent substrate on which are successively formed an anode layer, a hole injector (buffer) layer, a hole transport layer, an electroluminescent layer, an electron transport layer, an electron injection layer and an anode layer which may in turn be laminated to a second transparent substrate. Top emitting OLED's are also possible in which an aluminium or other metallic substrate carries an ITO layer, a hole injection layer, a hole transport layer, an electroluminescent layer, an electron transport layer, an electron injection layer and an ITO or other transparent cathode, light being emitted through the cathode. A further possibility is an inverted OLED in which a cathode of aluminium or aluminium alloyed with a low work function metal carries successively an electron injection layer, an electron transport layer, an electroluminescent layer, a hole transport layer, a hole injection layer and an ITO or other transparent conductive anode, emission of light being through the anode. If desired a hole blocking layer may be inserted e.g. between the electroluminescent layer and the electron transport layer.

OLEDs of the invention include small molecule OLEDs, polymer light emitting diodes (p-OLEDs), OLEDs that emit light by fluorescence, OLEDs that emit light by phosphorescence (PHOLEDs) and OLEDs that emit light by ion fluorescence (rare earth complexes) and include single-colour or multi-colour active or passive matrix displays.

Anode

In many embodiments the anode is formed by a layer of tin oxide or indium tin oxide coated onto glass or other transparent substrate. Other materials that may be used include antimony tin oxide and indium zinc oxide. If desired a modified anode may be produced e.g. by subsequently treating the ITO surface with oxygen plasma, and then conditioned as a modified anode by decomposing $CHF_3$ gas in a plasma treatment chamber to deposit an ~1-nm-thick layer of $CF_x$.

Hole Injection Materials

A single layer may be provided between the anode and the electroluminescent material, but in many embodiments there are at least two layers one of which is a hole injection layer (buffer layer) and the other of which is a hole transport layer, the two layer structure offering in some embodiments improved stability and device life (see U.S. Pat. No. 4,720,432 (VanSlyke et al., Kodak). The hole injection layer may serve to improve the film formation properties of subsequent organic layers and to facilitate the injection of holes into the hole transport layer.

Suitable materials for the hole injection layer which may be of thickness e.g. 0.1-200 nm depending on material and cell type include hole-injecting porphyrinic compounds—see U.S. Pat. No. 4,356,429 (Tang, Eastman Kodak) e.g. zinc phthalocyanine copper phthalocyanine and ZnTpTP, whose formula is set out below:

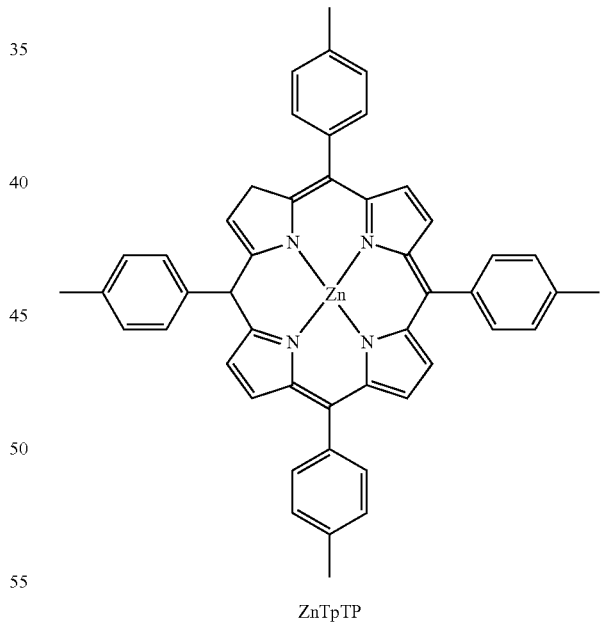

ZnTpTP

The hole injection layer may also be a fluorocarbon-based conductive polymer formed by plasma polymerization of a fluorocarbon gas—see U.S. Pat. No. 6,208,075 (Hung et al; Eastman Kodak), a triarylamine polymer—see EP-A-0891121 (Inoue et al., TDK Corporation) or a phenylenediamine derivative—see EP-A-1029909 (Kawamura et al., Idemitsu) or a material described in U.S. Pat. No. 6,436,559 (Ueno, Canon) and U.S. Pat. No. 6720573 (Se-Hwan, LG Chemical Co., Ltd.).

Hole-Transport Materials

Hole transport layers which may be used are preferably of thickness 20 to 200 nm.

One class of hole transport materials comprises polymeric materials that may be deposited as a layer by means of spin coating. Such polymeric hole-transporting materials include poly(N-vinylcarbazole) (PVK), polythiophenes, polypyrrole, and polyaniline. Other hole transporting materials are conjugated polymers e.g. poly (p-phenylenevinylene) (PPV) and copolymers including PPV. Other preferred polymers are: poly(2,5 dialkoxyphenylene vinylenes e.g. poly(2-methoxy-5-(2-methoxypentyloxy-1,4-phenylene vinylene), poly(2-methoxypentyloxy)-1,4-phenylenevinylene), poly(2-methoxy-5-(2-dodecyloxy-1,4-phenylenevinylene) and other poly (2,5 dialkoxyphenylenevinylenes) with at least one of the alkoxy groups being a long chain solubilising alkoxy group; polyfluorenes and oligofluorenes; polyphenylenes and oligophenylenes; polyanthracenes and oligoanthracenes; and polythiophenes and oligothiophenes.

A further class of hole transport materials comprises sublimable small molecules. For example, aromatic amines may be sued e.g. small molecules of the general formulae (a)-(g) below

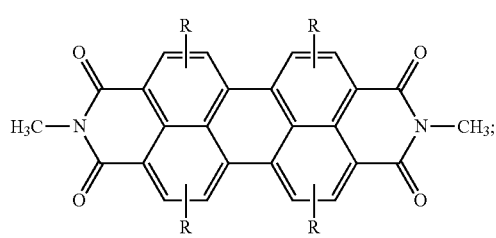
(a)

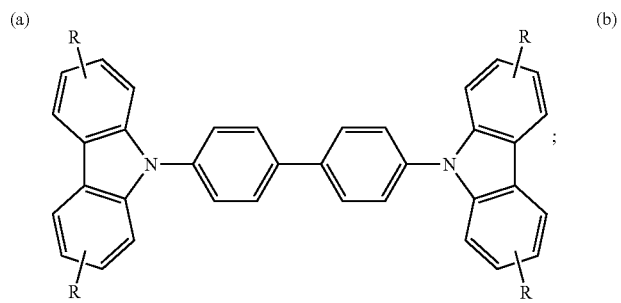
(b)

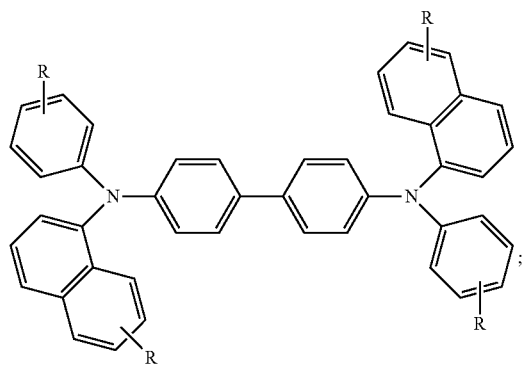
(c)

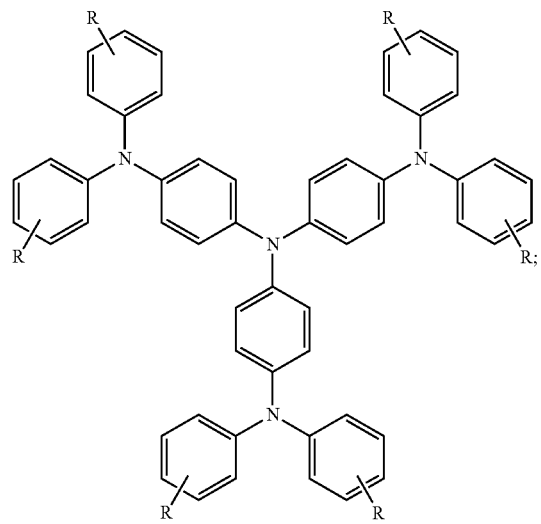
(d)

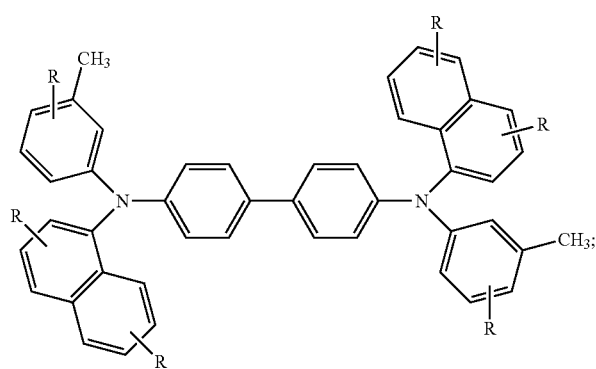
(e)

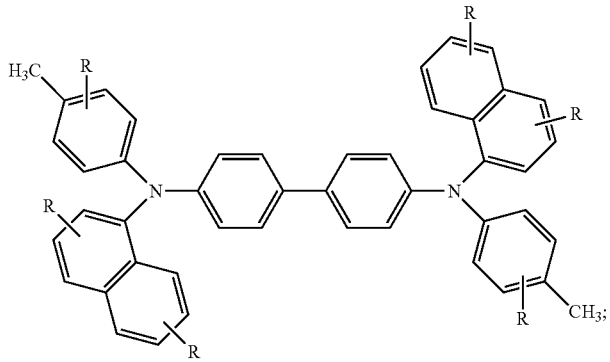
(f)

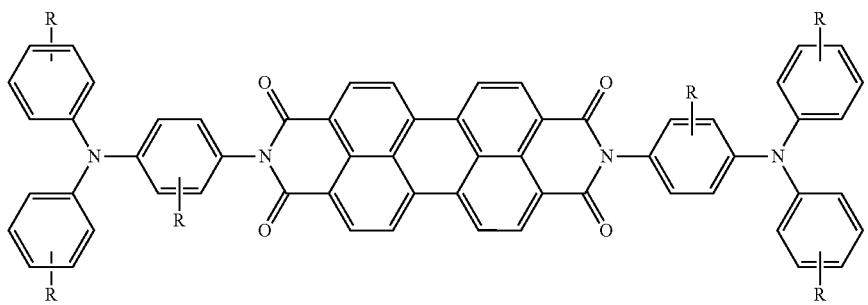
(g)

wherein the groups R in any of the formulae in (a) to (g) can be the same or different and are selected from hydrogen; substituted and unsubstituted aliphatic groups; substituted and unsubstituted aromatic, heterocyclic and polycyclic ring structures; halogens; and thiophenyl groups; and wherein in formula (a) the methyl groups may be replaced by $C_1$-$C_4$ alkyl or monocyclic or polyclic aryl or heteroraryl which may be further substituted e.g. with alkyl, aryl or arylamino.

Further hole transport materials comprise

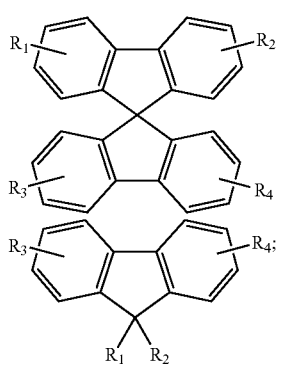

or wherein the groups $R_1$-$R_4$ when appearing in either of the above formulae can be the same or different and are selected from hydrogen; substituted and unsubstituted aliphatic groups; substituted and unsubstituted aromatic, heterocyclic and polycyclic ring structures; halogens; and thiophenyl groups.

Particular preferred hole-transport materials are. aromatic tertiary amines including at least two aromatic tertiary amine moieties (e.g. those based on biphenyl diamine or of a "starburst" configuration). of which the following are representative:

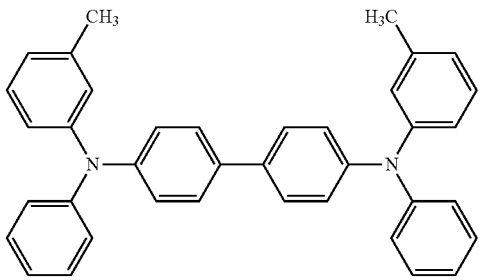

TPD
Tg (° C.) 61
$\mu h$ (cm$^2$ V$^{-1}$ s$^{-1}$) $1 \times 10^{-3}$

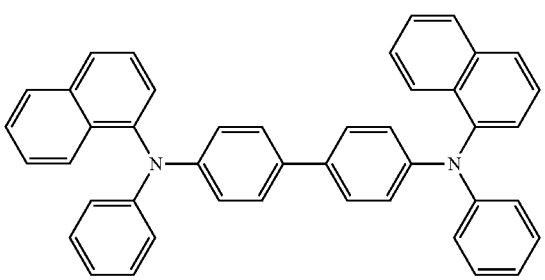

α-NBP
Tg (° C.) 98
$\mu h$ (cm$^2$ V$^{-1}$ s$^{-1}$) $1 \times 10^{-4}$

-continued

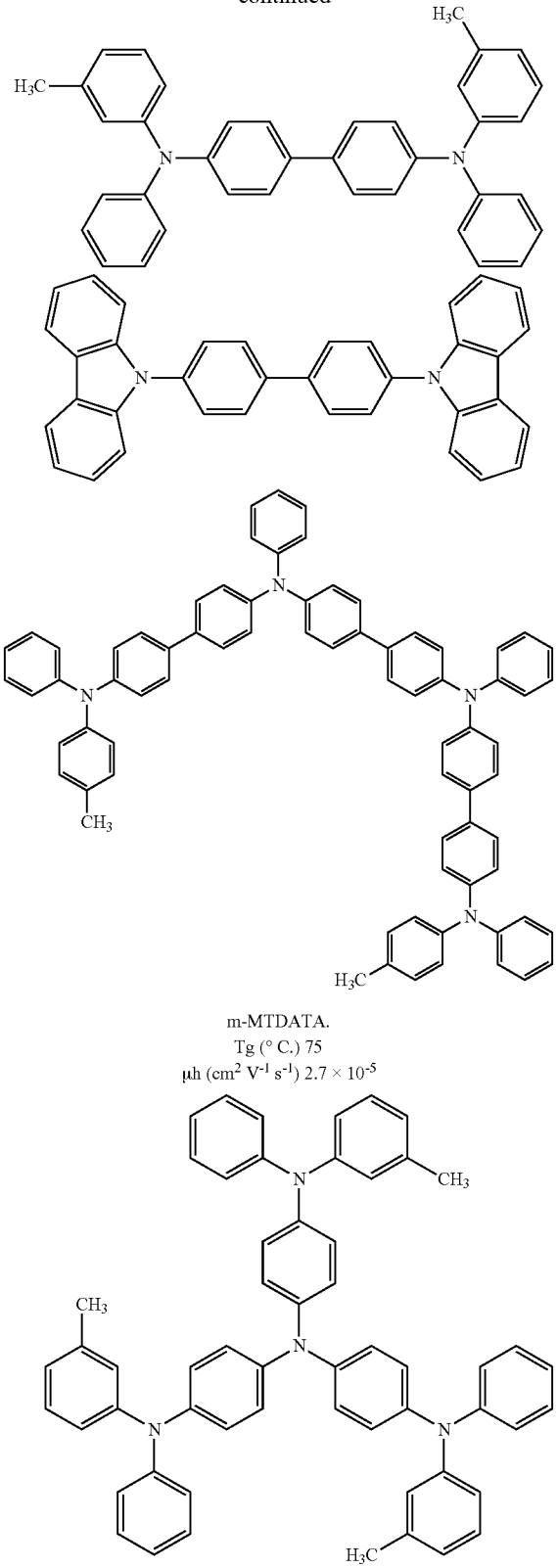

m-MTDATA.
Tg (° C.) 75
μh (cm² V⁻¹ s⁻¹) 2.7 × 10⁻⁵

A further possible material is 4,4',4"-tris(carbazolyl)-triphenylamine (TCTA) which is a hole transport material with a wider band gap than α-NBP and which can in some embodiments assist in confining excitation to the emissive layer.

It further includes spiro-linked molecules which are aromatic amines e.g. spiro-TAD (2,2',7,7'-tetrakis-(diphenylamino)-spiro-9,9'-bifluorene).

A further class of small molecule hole transport materials is disclosed in WO 2006/061594 (Kathirgamanathan et al) and is based on diamino dianthracenes. Typical compounds include:
9-(10-(N-(naphthalen-1-yl)-N-phenylamino)anthracen-9-yl)-N-(naphthalen-1-yl)-N-phenylanthracen-10-amine;
9-(10-(N-biphenyl-N-2-m-tolylamino)anthracen-9-yl)-N-biphenyl-N-2-m-tolylamino-anthracen-10-amine; and
9-(10-(N-phenyl-N-m-tolylamino)anthracen-9-yl)-N-phenyl-N-m-tolylanthracen-10-amine.

Electroluminescent Materials

In principle any electroluminescent material may be used. The electroluminescent layer may comprise as luminescent material a metal quino late, iridium, ruthenium, osmium, rhodium, iridium, palladium or platinum complex, a boron complex or a rare earth complex. It may include a molecular solid which may be a fluorescent dye e.g. a perylene dye, metal complexe e.g. Alq₃, so-called "blue" aluminium quino late of the type Alq₂L where q represents a quino late and L represents a mono-anionic aryloxy ligand e.g. bis(2-methyl-8-quinolinolato)(4-phenyl-phenolato) Al(III), Ir(III) L₃, lithium quinolate, titanium quinolate, zirconium quinolate or hafnium quonolate, a rare earth chelate e.g. a Tb(III) complex, a dendrimer or an oligomer e.g. sexithiophene, or a polymeric emissive material.

One preferred class of electroluminescent materials comprises host materials doped with one or more dyes which may be fluorescent, phosphorescent or ion-phosphorescent (rare earth). The use of the novel compounds described herein as host material also forms part of the invention and they may provide red, green and blue emitters when doped with appropriate dopants, in embodiments one or more than one dopant. The term "electroluminescent device" includes electrophosphorescent devices.

Preferably the host is doped with a minor amount of a fluorescent material as a dopant, preferably in an amount of 0.01 to 25% by weight of the doped mixture. As discussed in U.S. Pat. No. 4,769,292 (Tang et al., Kodak), the contents of which are included by reference, the presence of the fluorescent material permits a choice from amongst a wide latitude of wavelengths of light emission. In particular, as disclosed in U.S. Pat. No. 4,769,292 by blending with the organo metallic complex a minor amount of a fluorescent material capable of emitting light in response to hole-electron recombination, the hue of the light emitted from the luminescent zone, can be modified. In theory, if a host material and a fluorescent material could be found for blending which have exactly the same affinity for hole-electron recombination, each material should emit light upon injection of holes and electrons in the luminescent zone. The perceived hue of light emission would be the visual integration of both emissions. However, since imposing such a balance of host material and fluorescent materials is limiting, it is preferred to choose the fluorescent material so that it provides the favoured sites for light emission. When only a small proportion of fluorescent material providing favoured sites for light emission is present, peak intensity wavelength emissions typical of the host material can be entirely eliminated in favour of a new peak intensity wavelength emission attributable to the fluorescent material.

While the minimum proportion of fluorescent material sufficient to achieve this effect varies, in no instance is it necessary to employ more than about 10 mole percent fluorescent material, based of host material and seldom is it necessary to employ more than 1 mole percent of the fluorescent material.

On the other hand, limiting the fluorescent material present to extremely small amounts, typically less than about $10^{-3}$ mole percent, based on the host material, can result in retaining emission at wavelengths characteristic of the host material. Thus, by choosing the proportion of a fluorescent material capable of providing favoured sites for light emission, either a full or partial shifting of emission wavelengths can be realized. This allows the spectral emissions of the EL devices to be selected and balanced to suit the application to be served. In the case of fluorescent dyes, typical amounts are 0.01 to 5 wt %, for example 2-3 wt %. In the case of phosphorescent dyes typical amounts are 0.1 to 15 wt %. In the case of ion phosphorescent materials typical amounts are 0.01-25 wt % or up to 100 wt %.

Choosing fluorescent materials capable of providing favoured sites for light emission, necessarily involves relating the properties of the fluorescent material to those of the host material. The host can be viewed as a collector for injected holes and electrons with the fluorescent material providing the molecular sites for light emission. One important relationship for choosing a fluorescent material capable of modifying the hue of light emission when present in the host is a comparison of the reduction potentials of the two materials. The fluorescent materials demonstrated to shift the wavelength of light emission have exhibited a less negative reduction potential than that of the host. Reduction potentials, measured in electron volts, have been widely reported in the literature along with varied techniques for their measurement. Since it is a comparison of reduction potentials rather than their absolute values which is desired, it is apparent that any accepted technique for reduction potential measurement can be employed, provided both the fluorescent and host reduction potentials are similarly measured. A preferred oxidation and reduction potential measurement techniques is reported by R. J. Cox, *Photographic Sensitivity*, Academic Press, 1973, Chapter 15.

A second important relationship for choosing a fluorescent material capable of modifying the hue of light emission when present in the host is a comparison of the band-gap potentials of the two materials. The fluorescent materials demonstrated to shift the wavelength of light emission have exhibited a lower band gap potential than that of the host. The band gap potential of a molecule is taken as the potential difference in electron volts (eV) separating its ground state and first singlet state. Band gap potentials and techniques for their measurement have been widely reported in the literature. The band gap potentials herein reported are those measured in electron volts (eV) at an absorption wavelength which is bathochromic to the absorption peak and of a magnitude one tenth that of the magnitude of the absorption peak. Since it is a comparison of band gap potentials rather than their absolute values which is desired, it is apparent that any accepted technique for band gap measurement can be employed, provided both the fluorescent and host band gaps are similarly measured. One illustrative measurement technique is disclosed by F. Gutman and L. E. Lyons, *Organic Semiconductors*, Wiley, 1967, Chapter 5.

With host materials which are themselves capable of emitting light in the absence of the fluorescent material, it has been observed that suppression of light emission at the wavelengths of emission characteristics of the host alone and enhancement of emission at wavelengths characteristic of the fluorescent material occurs when spectral coupling of the host and fluorescent material is achieved. By "spectral coupling" it is meant that an overlap exists between the wavelengths of emission characteristic of the host alone and the wavelengths of light absorption of the fluorescent material in the absence of the host. Optimal spectral coupling occurs when the emission wavelength of the host is within ±25 nm of the maximum absorption of the fluorescent material alone. In practice advantageous spectral coupling can occur with peak emission and absorption wavelengths differing by up to 100 nm or more, depending on the width of the peaks and their hypsochromic and bathochromic slopes. Where less than optimum spectral coupling between the host and fluorescent materials is contemplated, a bathochromic as compared to a hypsochromic displacement of the fluorescent material produces more efficient results.

Useful fluorescent materials are those capable of being blended with the host and fabricated into thin films satisfying the thickness ranges described above forming the luminescent zones of the EL devices of this invention. While crystalline organometallic complexes do not lend themselves to thin film formation, the limited amounts of fluorescent materials present in the host permit the use of fluorescent materials which are alone incapable of thin film formation. Preferred fluorescent materials are those which form a common phase with the host. Fluorescent dyes constitute a preferred class of fluorescent materials, since dyes lend themselves to molecular level distribution in the host. Although any convenient technique for dispersing the fluorescent dyes in the host can be used preferred fluorescent dyes are those which can be vacuum vapour deposited along with the host materials.

One class of host materials comprises metal complexes e.g. metal quinolates such as lithium quinolate, aluminium quinolate, titanium quinolate, zirconium quinolate or hafnium quinolate which may be doped with fluorescent materials or dyes as disclosed in patent application WO 2004/058913.

In the case of hosts which comprise quinolates e.g. aluminium quinolate or "blue" quinolates, see e.g. J. C. Deaton et al., *Inorg. Chim. Acta* (2007), doi:10.1016/j.ica.2007.07.008, the contents of which are incorporated herein by reference:

(a) the compounds below, for example, can serve as red dopants:

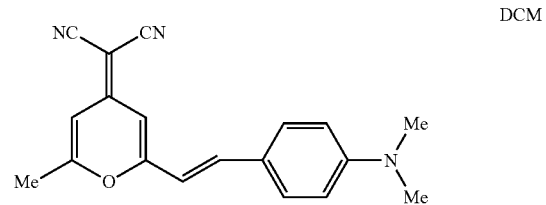

DCM

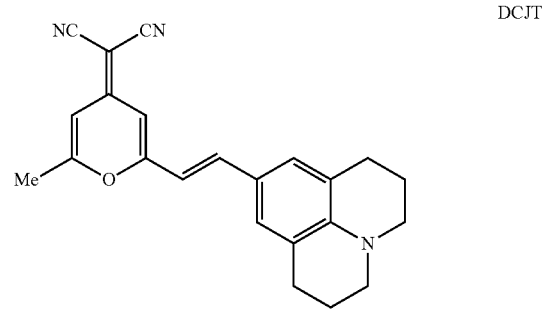

DCJT

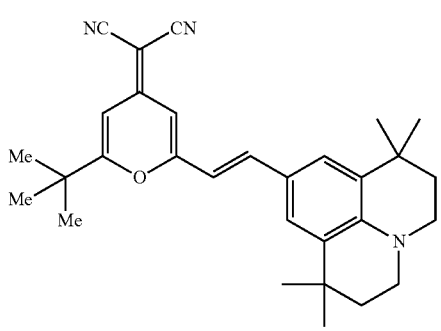
DCJTi

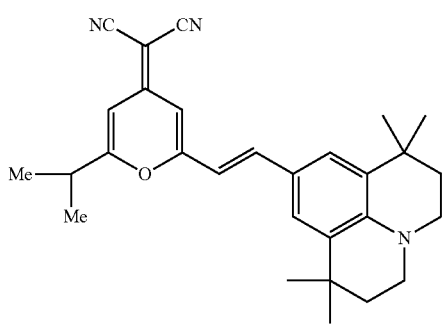
DCJTB (b) the compounds below, for example can serve as green dopants:

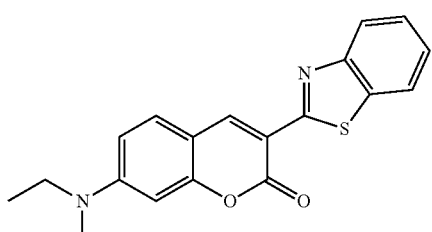

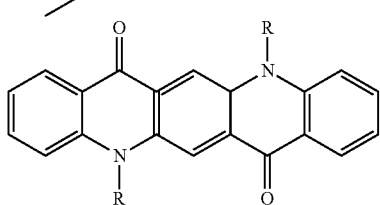

wherein R is $C_1$-$C_4$ alkyl, monocyclic aryl, bicycic aryl, monocyclic heteroaryl, bicyclic heteroaryl, aralkyl or thienyl, preferably phenyl; and (c) for biphenyloxy aluminium bis-quinolate ($BAlQ_2$) or aluminium quinolate the compounds perylene and 9-(10-(N-(naphthalen-8-yl)-N-phenylamino)anthracen-9-yl)-N-(naphthalen-8-yl)-N-phenylanthracen-10-amine can serve as a blue dopants.

Another preferred class of hosts is small molecules incorporating conjugated aromatic systems with e.g. 4-10 aryl or heteroaryl rings which may bear substituents e.g. alkyl (especially methyl), alkoxy and fluoro and which may also be doped with fluorescent materials or dyes.

An example of a system of the above kind is a blue-emitting material based on the following compound (Compound H) as host

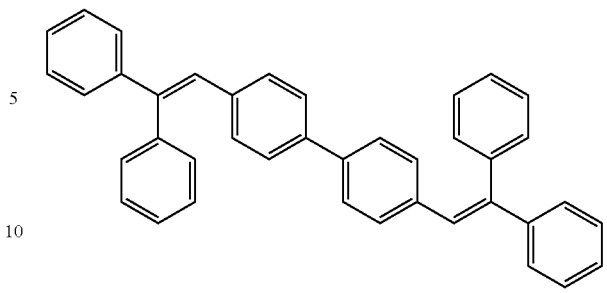

and perylene or 9-(10-(N-(naphthalen-8-yl)-N-phenylamino)anthracen-9-yl)-N-(naphthalen-8-yl)-N-phenylanthracen-10-amine as dopant. Further examples of host materials which are small aromatic molecules are shown below:

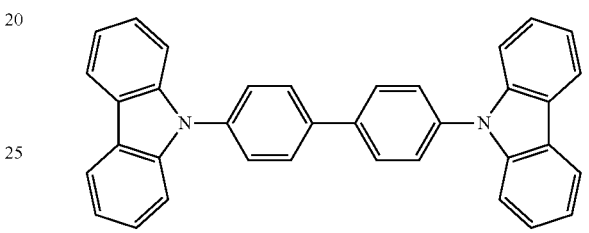
CBP

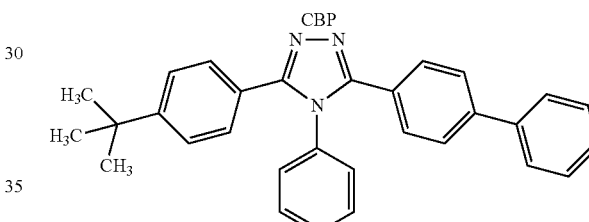
TAZ

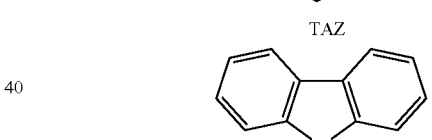

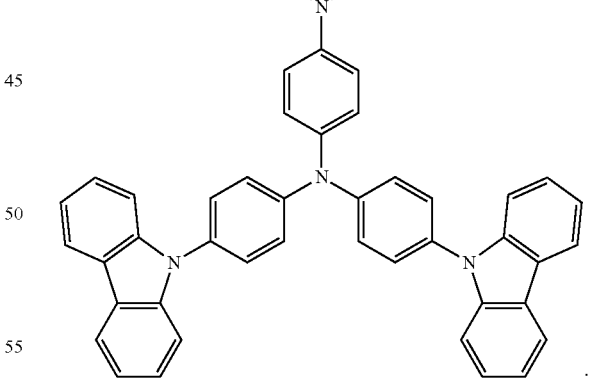
TCTA 2,9-Bis(2-thiophen-2-yl-vinyl)-[1,10]phenanthroline may, as explained above, may be used as host in the electroluminescent layer or may be present on its own.

Blue-emitting materials may be based on an organic host (e.g. a conjugated aromatic compound as indicated above) and diarylamine anthracene compounds disclosed in WO 2006/090098 (Kathirgamanathan et al.) as dopants. For example, CBP may be doped with blue-emitting substituted anthracenes inter alia 9,10-bis(-4-methylbenzyl)-anthracene, 9,10-bis-(2,4-dimethylbenzyl)-anthracene, 9,10-bis-(2,5-dimethylbenzyl)-anthracene, 1,4-bis-(2,3,5,6-tetramethylbenzyl)-anthracene, 9,10-bis-(4-methoxybenzyl)-anthracene, 9,10-bis-(9H-fluoren-9-yl)-anthracene, 2,6-di-t-butylanthracene, 2,6-di-t-butyl-9,10-bis-(2,5-dimethylbenzyl)-anthracene and 2,6-di-t-butyl-9,10-bis-(naphthalene-1-ylmethyl)-anthracene.

Further blue-emitting materials may employ TCTA as host and it may be doped with the blue phosphorescent materials set out below, see WO 2005/080526 (Kathirgamanathan et al.):

Blue Phosphorescent Materials

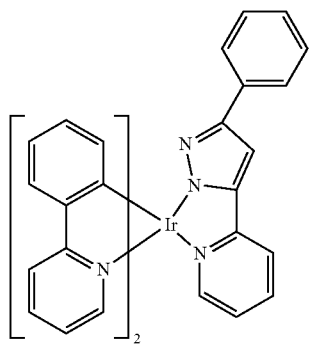

λmax 495 nm (DCM)

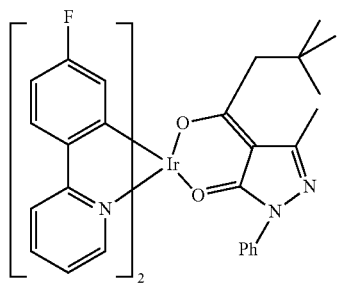

λmax 493 nm (DCM)

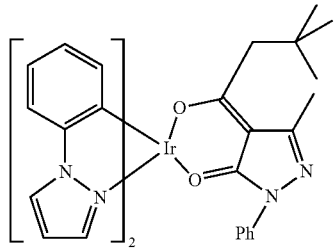

λmax 485 nm (DCM)

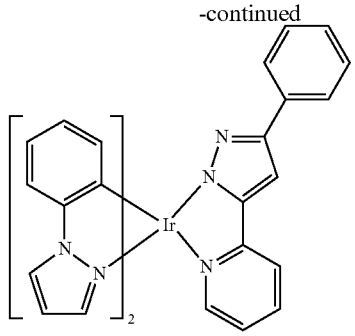

λmax 485 nm (DCM)

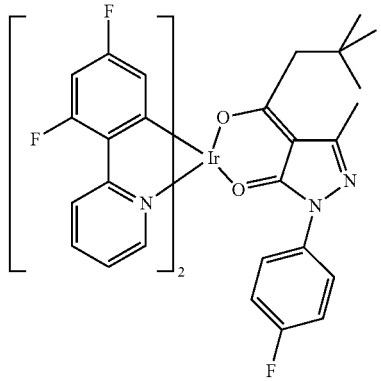

λmax 484 nm (DCM)

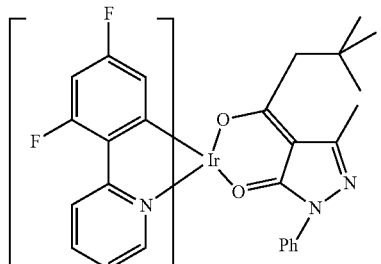

λmax 483 nm (DCM)

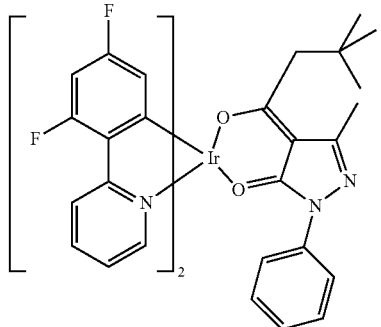

λmax 480 nm (DCM)

17
-continued
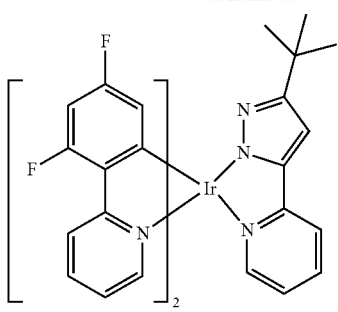
λmax 479 nm (DCM)
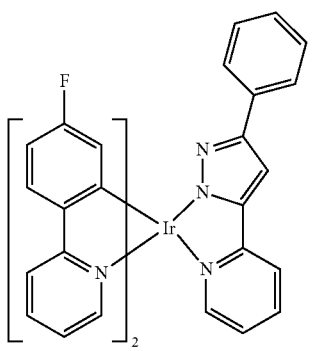
λmax 477 nm (DCM)
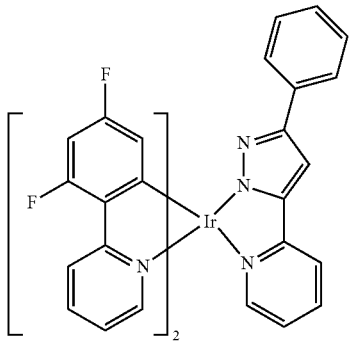
λmax 470 nm (DCM)
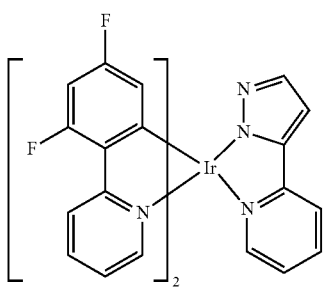
λmax 469, 493 nm (DCM)
18
-continued
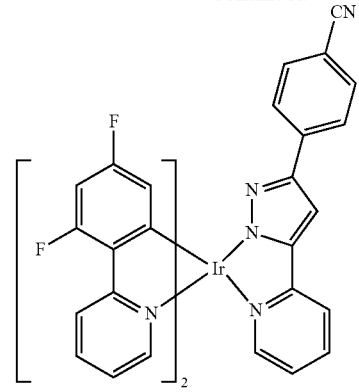
λmax 468 nm (DCM)
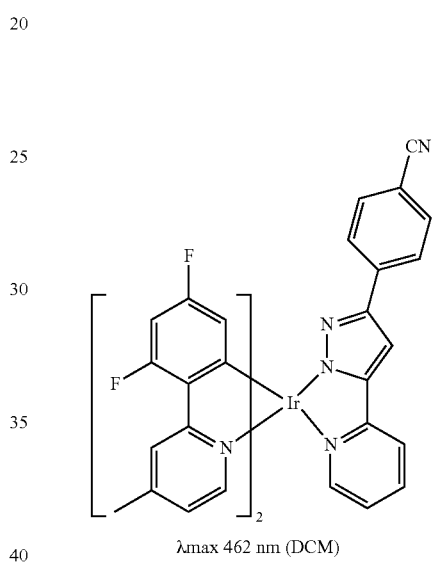
λmax 462 nm (DCM)
Examples of green phosphorescent materials that may be employed with CBP or TAZ are set out below (see WO 2005/080526):
Green Phosphorescent Materials
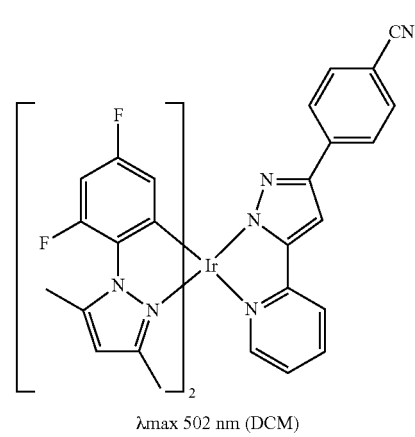
λmax 502 nm (DCM)

-continued
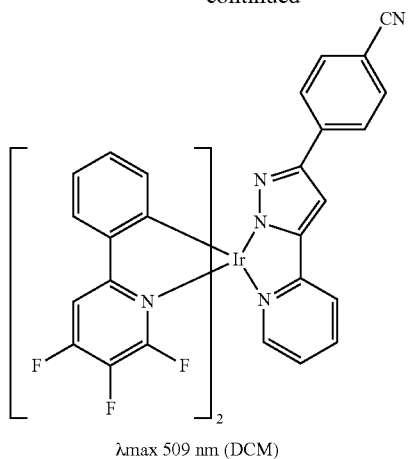
λmax 509 nm (DCM)
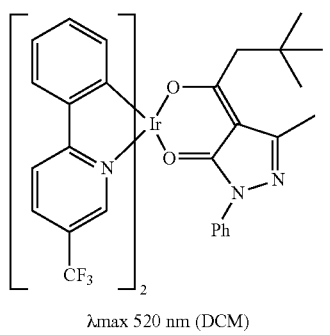
λmax 520 nm (DCM)
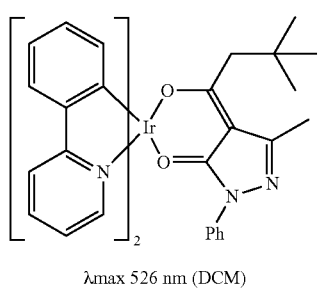
λmax 526 nm (DCM)
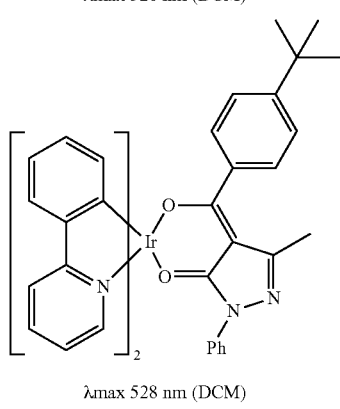
λmax 528 nm (DCM)
Examples of red phosphorescent materials that may be employed with CBP or TAZ are set out below (see WO 2005/080526):
Red Phosphorescent Materials
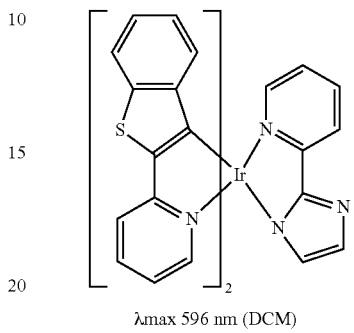
λmax 596 nm (DCM)
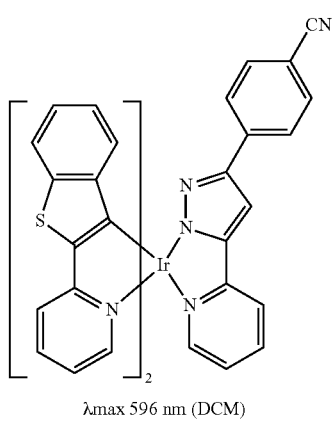
λmax 596 nm (DCM)
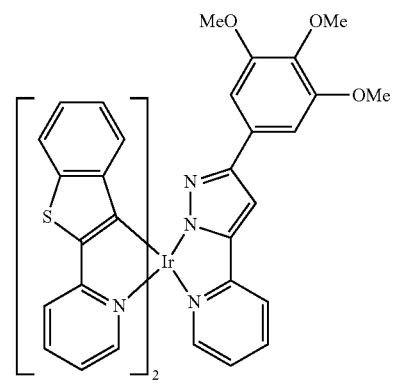
λmax 597 nm (DCM)

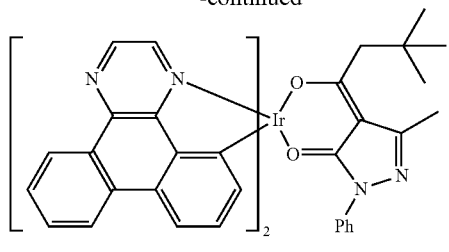
λmax 600 nm (DCM)

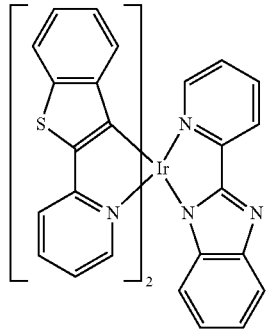
λmax 604 nm (DCM)

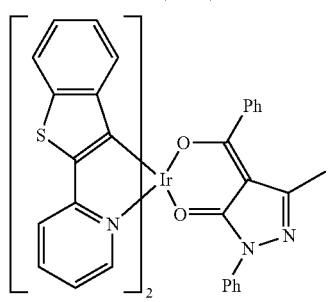
λmax 614 nm (DCM)

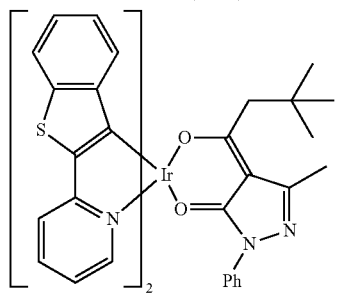
λmax 615 nm (DCM)

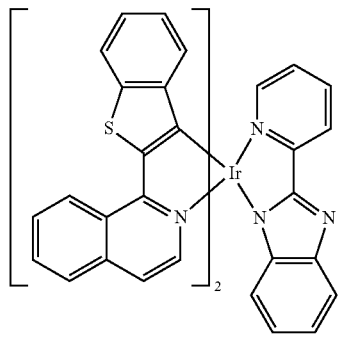
λmax 682 nm (DCM)

As further dopants, fluorescent laser dyes are recognized to be useful fluorescent materials for use in the organic EL devices. Dopants which can be used include diphenylacridine, coumarins, perylene and their derivatives. Useful fluorescent dopants are disclosed in U.S. Pat. No. 4,769,292. One class of preferred dopants is coumarins. The following are illustrative fluorescent coumarin dyes known to be useful as laser dyes:

FD-1 7-Diethylamino-4-methylcoumarin,
FD-2 4,6-Dimethyl-7-ethylaminocoumarin,
FD-3 4-Methylumbelliferone,
FD-4 3-(2'-Benzothiazolyl)-7-diethylaminocoumarin,
FD-5 3-(2'-Benzimidazolyl)-7-N,N-diethylaminocoumarin,
FD-6 7-Amino-3-phenylcoumarin,
FD-7 3-(2'-N-Methylbenzimidazolyl)-7-N,N-diethylaminocoumarin,
FD-8 7-Diethylamino-4-trifluoromethylcoumarin,
FD-9 2,3,5,6-1H,4H-Tetrahydro-8-methylquinolazino[9,9a,1-gh]coumarin,
FD-10 Cyclopenta[c]julolindino[9,10-3]-11H-pyran-11-one,
FD-11 7-Amino-4-methylcoumarin,
FD-12 7-Dimethylaminocyclopenta[c]coumarin,
FD-13 7-Amino-4-trifluoromethylcoumarin,
FD-14 7-Dimethylamino-4-trifluoromethylcoumarin,
FD-15 1,2,4,5,3H,6H,10H-Tetrahydro-8-trifluoromethyl[1]benzopyrano[9,9a,1-gh]quinolizin-10-one,
FD-16 4-Methyl-7-(sulfomethylamino)coumarin sodium salt,
FD-17 7-Ethylamino-6-methyl-4-trifluoromethylcoumarin,
FD-18 7-Dimethylamino-4-methylcoumarin,
FD-19 1,2,4,5,3H,6H,10H-Tetrahydro-carbethoxy[1]benzopyrano[9,9a,1-gh]quinolizino-10-one,
FD-20 9-Acetyl-1,2,4,5,3H,6H,10H-tetrahydro[1]benzopyrano[9,9a,1-gh]quinolizino-10-one,
FD-21 9-Cyano-1,2,4,5,3H,6H,10H-tetrahydro[1]benzopyrano[9,9a,1-gh]quinolizino-10-one,
FD22 9-(t-Butoxycarbonyl)-1,2,4,5,3H,6H,10H-tetrahyro[1]-benzopyrano-[9,9a,1-gh]quinolizino-10-one,
FD-23 4-Methylpiperidino[3,2-g]coumarin,
FD-24 4-Trifluoromethylpiperidino[3,2-g]coumarin,
FD-25 9-Carboxy-1,2,4,5,3H,6H,10H-tetrahydro[1]benzopyrano[9,9a,1-gh]quinolizino-10-one,
FD-26 N-Ethyl-4-trifluoromethylpiperidino[3,2-g]coumarin.

Other dopants include salts of bis benzene sulphonic acid (require deposition by spin-coating rather than sublimation) such as (C)

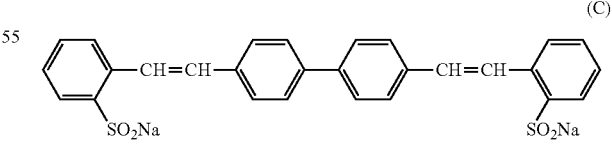

and perylene and perylene derivatives and dopants. Other dopants are dyes such as the fluorescent 4-dicyanomethylene-4H-pyrans and 4-dicyanomethylene-4H-thiopyrans, e.g. the fluorescent dicyanomethylenepyran and thiopyran dyes. Useful fluorescent dyes can also be selected from among known polymethine dyes, which include the cyanines, complex cyanines and merocyanines (i.e. tri-, tetra- and poly-nuclear cyanines and merocyanines), oxonols, hemioxonols, styryls, merostyryls, and streptocyanines. The cyanine dyes include, joined by a methine linkage, two basic heterocyclic nuclei, such as azolium or azinium nuclei, for example, those derived from pyridinium, quinolinium, isoquinolinium, oxazolium, thiazolium, selenazolium, indazolium, pyrazolium, pyrrolium, indolium, 3H-indolium, imidazolium, oxadiazolium, thiadioxazolium, benzoxazolium, benzothiazolium, benzoselenazolium, benzotellurazolium, benzimidazolium, 3H- or 1H-benzoindolium, naphthoxazolium, naphthothiazolium, naphthoselenazolium, naphthotellurazolium, carbazolium, pyrrolopyridinium, phenanthrothiazolium, and acenaphthothiazolium quaternary salts. Other useful classes of fluorescent dyes are 4-oxo-4H-benz-[d,e]anthracenes and pyrylium, thiapyrylium, selenapyrylium, and telluropyrylium dyes.

Further blue-emitting materials are disclosed in the following patents, applications and publications, the contents of which are incorporated herein by reference:

U.S. Pat. No. 5,141,671 (Bryan, Kodak)—Aluminium chelates containing a phenolato ligand and two 8-quinolinolato ligands.

WO 00/32717 (Kathirgamanathan)—Lithium quinolate which is vacuum depositable, and other substituted quinolates of lithium where the substituents may be the same or different in the 2,3,4,5,6 and 7 positions and are selected from alky, alkoxy, aryl, aryloxy, sulphonic acids, esters, carboxylic acids, amino and amido groups or are aromatic, polycyclic or heterocyclic groups.

US 2006/0003089 (Kathirgamanathan)—Lithium quinolate made by reacting a lithium alkyl or alkoxide with 8-hydroxyquinoline in acetonitrile.

Misra, http://www.ursi.org/Proceedings/ProcGA05/pdf/D04.5(01720).pdf Blue organic electroluminescent material bis-(2-methyl 8-quinolinolato) (triphenyl siloxy)aluminium (III) vacuum depositable at $1 \times 10^{-5}$ Torr.

WO 03/006573 (Kathirgamanathan et al)—Metal pyrazolones.

WO 2004/084325 (Kathirgamanathan et al)—Boron complexes.

WO 2005/080526 (Kathitgamanathan et al)—Blue phosphorescent iridium-based complexes.

Ma et al., *Chem. Comm.* 1998, 2491-2492 Preparation and crystal structure of a tetranuclear zinc(II) compound [$Zn_4O$(AID)$_6$] with 7-azaindolate as a bridging ligand. Fabrication of inter alia a single-layer LED by vacuum deposition of this compound (<200° C., $2 \times 10^{-6}$ Torr) onto a glass substrate coated with indium-tin oxide to form a thin homogeneous film was reported.

Further electroluminescent materials which can be used include metal quinolates such as aluminium quinolate, lithium quinolate, titanium quinolate, zirconium quinolate, hafnium quinolate etc.

Many further electroluminescent materials that may be used are disclosed in WO 2004/050793 (pyrazolones), WO 2004/058783 (diiridium metal complexes), WO 2006/016193 (dibenzothiophenyl metal complexes) and WO 2006/024878 (thianthrene metal complexes); see also WO 2006/040593 the contents of which are incorporated herein by reference. Rare earth chelates, in particular may be employed as green and red emitters. Furthermore, there may be used as electroluminescent materials conducting polymers e.g. polyaniline, phenylene vinylene polymers, fluorene homopolymers and copolymers, phenylene polymers, as indicated below:

Conducting Polymers

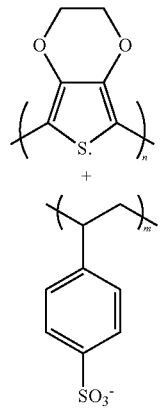

PEDOT-PSS ($\sigma = 1$ S cm$^{-1}$)

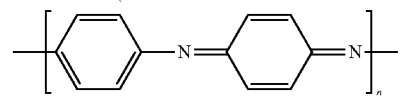

Polyaniline (PANI) ($\sigma = 1\text{-}10$ S cm$^{-1}$)

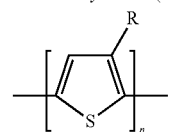

Polythiophene (PT)
($\sigma = 1\text{-}500$ S cm$^{-1}$)

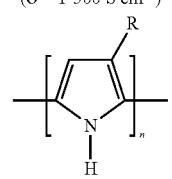

Polypyrrole (PPy)
($\sigma = 1\text{-}100$ S cm$^{-1}$)

Mixed host materials have also been disclosed in the literature and may be used in OLEDs devices according to the invention.

Various references disclose additives and mixed hosts for OLED's in an attempt to further improve properties. Jarikov et al., *J. Appl. Phys.*, 100, 014901 (2006) discloses flat and rigid polycyclic aromatic hydrocarbons (PAHs) as LEL additives e.g. perylene. Jarikov et al. further report J. Appl. Phys., 100, pp. 094907-094907-7 (2006) perylene derivatives as light-emitting-layer (LEL) additives in organic light-emitting diodes (OLEDs). These molecules readily form emissive aggregates when added to the LEL. Addition of these polycyclic aromatic hydrocarbons increases the half-life ($t_{50}$) of undoped and doped OLEDs by 30-150 times e.g. in an Alq$_3$+ dibenzo[b,k]perylene mixed host. The authors yet further report in *J. Appl. Phys.*, 102, 104908 (2007) a synergistic effect of a lifetime-extending light-emitting-layer (LEL) additive and improved electron injection and transport in organic light-emitting diodes (OLEDs). Di-(2-naphthyl) perylene (DNP) serves as a LEL additive said to extend the operating lifetime of OLEDs by over two orders of magnitude. Using 2-phenyl-9,10-di(2-naphthyl)anthracene (PADN) as an electron-transport layer (ETL) and a separate layer of 4,7-diphenyl-1,10-phenanthroline (BPhen) as an electron-injection layer (EIL) the authors claimed to have significantly improved electron delivery into the charge recombination zone relative to traditional ETL made of tris (8-quinolinolate)aluminium (Alq). See also U.S. Pat. No. 7,175,922 (Jarikov et al) the disclosure of which is incorporated herein by reference. J. C. Deaton et al (supra) disclose an α-NBP host with a "blue" aluminium quinolate as co-host and an iridium dopant. Very good yields were obtained with low concentrations of dopant for phosphorescent devices and it was found that the mixed host device provided increased power efficiency. It was hypothesized that the explanation was a reduction in the energy barrier to inject holes into the emissive layer by mixing the hole-transporting NPB having an ionization potential of 5.40 eV into the dominantly electron-transporting "blue" aluminium quinolate, having a higher ionization potential of 6.02 eV.

U.S. Pat. No. 6,392,250 (Aziz et al, the disclosure of which is incorporated herein by reference.) discloses organic light emitting devices comprising a mixed region comprising a mixture of a hole transport material e.g. an aromatic tertiary amine, an electron transport material e.g. a quinolate and a dopant material. For example N,N'-di-1-naphthyl-N,N'-diphenyl-1,1'-biphenyl-1,1'-biphenyl-4,4'-diamine (NPB), and tris(8-hydroxyquinoline) aluminium ($Alq_3$) may be used as the hole transport material and the electron transport material, respectively and N,N'-dimethylquinacridone (DMQ), 5,6,11,12-tetraphenylnapthacene (Rubrene), and Nile-red dye (available from Aldrich Chemicals of Milwaukee, Wis.) may be used as dopants.

US 2002/0074935 (Kwong et al) also discloses devices with an emissive layer containing PtOEP or bis(benzothienyl-pyridinato-NAC)Iridium(III) (acetylacetonate) as a dopant and equal proportions of NPB and Alq as host materials. It is explained that the mixed host electroluminescent mixed layer serves to substantially reduce the accumulation of charge that is normally present at the heterojunction interface of heterostructure devices, thereby reducing organic material decomposition and enhancing device stability and efficiency.

In US 2004/0155238 (Thompson et al.) a light emitting layer of the OLED device contains a wide band gap inert host matrix in combination with a charge carrying material and a phosphorescent emitter. The charge carrying compound can transport holes or electrons, and it is selected so that charge carrying material and phosphorescent emitter transport charges of opposite polarity.

M. Furugori et al. in US 2003/0141809 disclose phosphorescent devices where a host material is mixed with another hole- or electron transporting material in the light emitting layer. The document discloses that devices utilizing plural host compounds show higher current and higher efficiencies at a given voltage.

T. Igarashi et al. in WO 2004/062324 disclose phosphorescent devices with the light emitting layer containing at least one electron transporting compound, at least one hole transporting compound and a phosphorescent dopant.

WO 2006/076092 (Kondakova et al., the contents of which are also incorporated herein by reference) discloses OLED device comprising a cathode, an anode, and located therebetween a light emitting layer (LEL) comprising at least one hole transporting co-host e.g. an aromatic tertiary amine such as 4,4'-Bis[N-(1-naphthyl)-N-phenylamino]biphenyl (NPB), 4,4'-Bis[N-(1-naphthyl)-N-(2-naphthyl)amino]biphenyl (TNB), 4,4'-Bis[N-(3-methylphenyl)-N-phenylamino-]biphenyl (TPD), 4,4'-Bis-diphenylamino-terphenyl or 2,6,2',6'-tetramethyl-N,N,N',N'-tetraphenyl-benzidine. and at least one electron transporting co-host e.g. a substituted 1,2,4-triazole such as 3-phenyl-4-(1-naphtyl)-5-phenyl-1,2,4-triazole or a substituted 1,3,5-triazine such as 2,4,6-tris(diphenylamino)-1,3,5-triazine, 2,4,6-tricarbazolo-1,3,5-triazine, 2,4,6-tris(N-phenyl-2-naphthylamino)-1,3,5-triazine, 2,4,6-tris(N-phenyl-1-naphthylamino)-1,3,5-triazine and 4,4',6,6'-tetraphenyl-2,2'-bi-1,3,5-triazine together with a phosphorescent emitter, wherein the triplet energy of each of the co-host materials is greater than the triplet energy of the phosphorescent emitter, and further containing an exciton blocking layer comprising a hole transporting material with triplet energy greater or equal to 2.5 eV adjacent the emitting layer on the anode side, which may be a substituted triarylamine e.g. 4,4',4"-tris[(3-methylphenyl)phenylamino]triphenylamine (MTDATA), 4,4',4"-tris(N,N-diphenyl-amino) triphenylamine (TDATA), N,N-bis[2,5-dimethyl-4-[(3-methylphenyl)-phenylamino]phenyl]-2,5-dimethyl-N'-(3-methylphenyl)-N'-phenyl-1,4-benzenediamine. The devices are said to exhibit improved efficiency and reduced drive voltage.

U.S. Pat. No. 7,045,952 (Lu, Universal Display Corporation) discloses an organic light emissive device comprising an emissive region disposed between and electrically connected to an anode and a cathode, wherein the emissive region comprises (i) a first single-host emissive layer, comprising a first host material, and (ii) a mixed-host emissive layer in direct contact with the first single-host emissive layer, wherein the mixed-host emissive layer comprises the first host material, and a second host material, and wherein the first single-host emissive layer and the mixed-host emissive layer each further comprise a phosphorescent emissive material.

Electron Transport Material

As explained, the compounds set out above can be comprised in the electron transport layer as a component thereof or providing the layer in its entirety. Preferably the content of compound as set out above in the ET layer is at least 30 wt %, preferably at least 50 wt %. They may be used alone, may be doped e.g. with a low work function metal or with a complex of a low work function metal or they may be used in admixture with other known electron transport materials.

The compounds of the invention may be used in admixture with other small molecule electron transport materials e.g. those disclosed by Kulkarni et al., supra. They may, for example be used in electron transport layers that also comprise a quinolate or substituted quinolate e.g aluminium or zirconium quinolate or 2-methylquinolate, or e.g. a phenanthroline compound e.g. bathophen and 4,7-diphenyl-1,10-phenanthroline.

A preferred genus of phenanthrolines the subject of WO 2008/078115 (Kathirgamanathan et al.) comprises compounds of formula

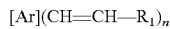

wherein n is an integer from 1 to 4; [Ar] is a polycyclic aromatic or heteroaromatic scaffold e.g a phenanthroline scaffold optionally substituted with one or more alkyl or alkoxy groups; and $R_1$ is a 5-membered heteroaryl group optionally substituted with methyl, methoxy, aryl or heteroaryl, or is phenyl or naphthyl optionally substituted with methyl, methoxy, trifluoromethyl or cyano or is biphenyl or is substituted biphenyl. Representative compounds include 2,9-bis(4,4'-trifluoromethyl styrenyl)phenenthroline, 2,9-bis ((E)-2-(5-(thiophen-2-yl)thiophen-2-yl)vinyl)-1,10-phenanthroline, 2,9-bis(4,4'-cyanostyrenyl)phenanthroline and 2,9-bis(2,2'-Vinyl-5,5'-phenyl thiophenyl)phenanthroline.

Where the present compounds are used in combination with existing electron transporters they may be used in relative amounts of e.g. about 1:1 by weight or the present compounds may be the major component.

Dopants e.g. a low work function metal such as lithium, caesium or potassium may be present. In the case of a multi-component electron transport layer the various components of the layer may be co-deposited by vacuum vapour deposition.

The compounds of the invention may be used in association with aromatic nitrogen containing small molecule hole transport materials e.g. of formulae (a) to (g) above which when incorporated into an electron transport material in small amounts e.g. 0.01-10 wt % are electron donating through the lone electron pair on the nitrogen atoms.

Compounds of the formula are as set out above may also be mixed any of the compounds claimed in our International application WO 2008/081178, the contents of which are incorporated herein by reference. Such compounds are of the formula

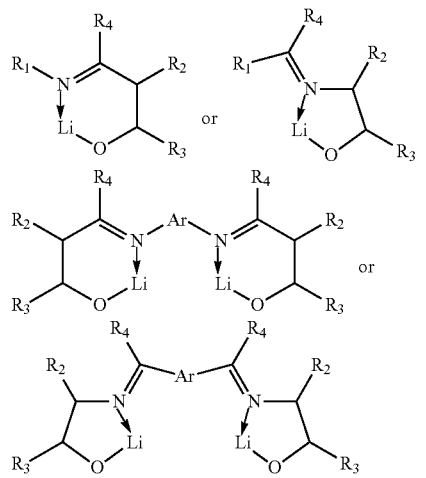

wherein $R_1$ is a 1-5 ring aryl (including polycyclic), aralkyl or heteroaryl group which may be substituted with one or more $C_1$-$C_4$ alkyl, alkoxy or cyano;

$R_2$ and $R_3$ together form a 1-5 ring aryl (including polycyclic), aralkyl or heteroaryl group which may be substituted with $C_1$-$C_4$ alkyl, alkoxy or cyano;

$R_4$ is hydrogen, $C_1$-$C_4$ alkyl or aryl; and

Ar is monocyclic, bicyclic or tricyclic aryl or heteroaryl which may be substituted with one or more $C_1$-$C_4$-alkyl or alkoxy groups, or an oligomer thereof. A preferred sub-genus of compounds is of formula

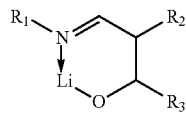

wherein $R_1$ is phenyl or phenyl substituted with one or more $C_1$-$C_4$ alkyl groups and $R_2$ and $R_3$ together form phenyl or phenyl substituted by one or more $C_1$-$C_4$ alkyl groups.

Compounds of the above formula in which $R_4$ is hydrogen may be made by reacting a primary aromatic or heteroaromatic amine with an aromatic or heteroaromatic aldehyde to form a Schiff base, followed by reaction of the Schiff base with a lithium compound e.g. a lithium alkoxide e.g. lithium t-butoxide. Compounds of the above formula in which $R_4$ is alkyl, aryl or heteroaryl may be made similarly starting from a secondary aromatic or heteroaromatic amine.

Vacuum sublimable compounds within the above genus include

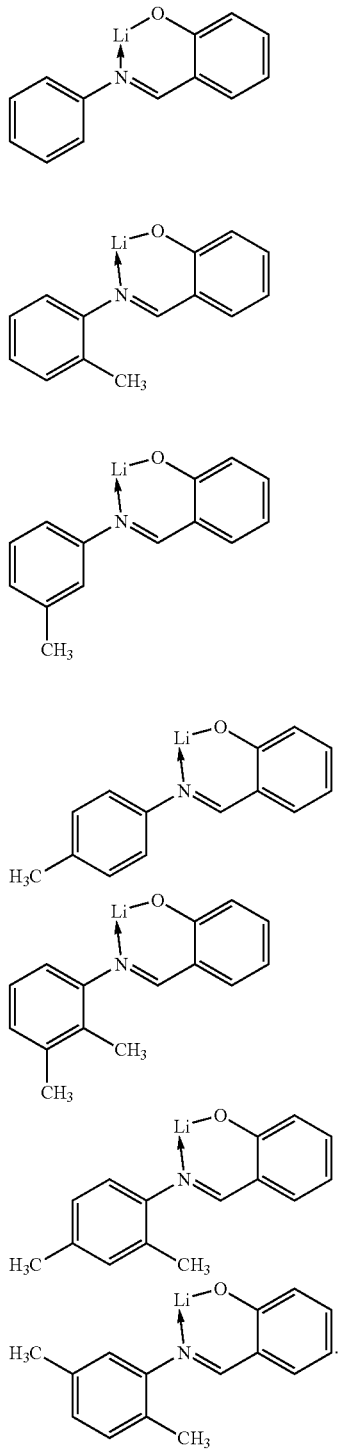

Other compounds which are solution-processable include the following:

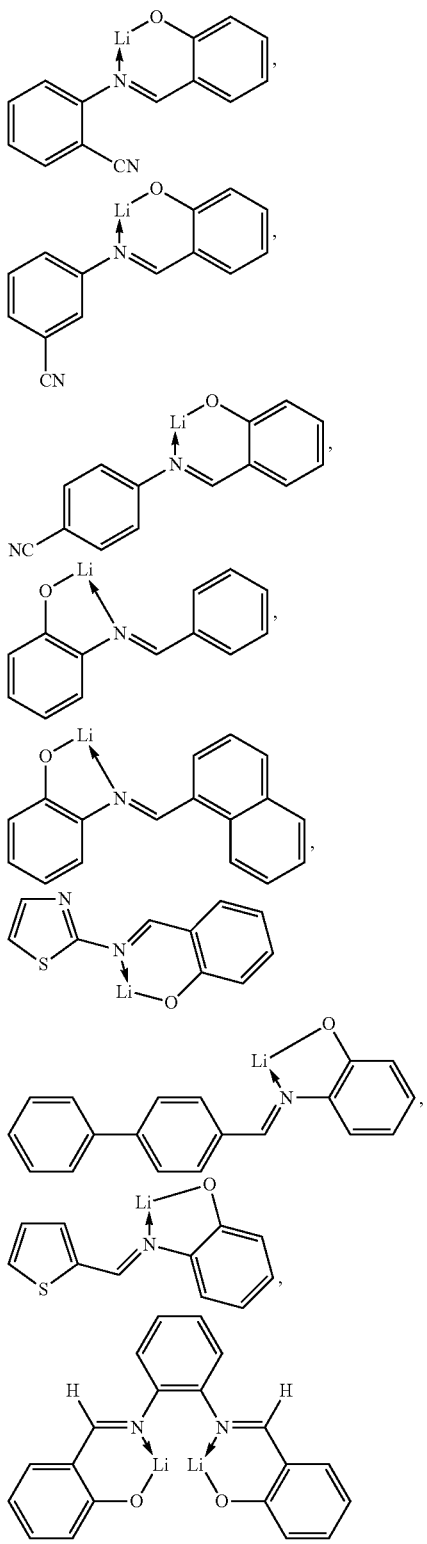

Electron Injection Material

Any known electron injection material may be used, LiF being typical. Other possibilities include $BaF_2$, $CaF_2$ and $CsF_2$. A further class of electron injectors comprises sublimable or coatable e.g. spin-coatable small molecules with electron injection properties. A layer of small molecule electron injection material is preferably about 0.3 nm in thickness and preferably has a work function of less than magnesium 3.7 eV, this being regarded for present purposes as a low work function. In some embodiments the electron injection material may be doped with a low work function metal e.g. lithium, potassium or caesium. In the case of a lithium-based small molecule electron injection material, doping may be with metallic lithium.

Metal quinolates can lower the work function of the cathode, enable the electroluminescent device to operate at a lower voltage and improve the lifetime and performance of the device. In some embodiments quinolates have been found superior to the previously used lithium fluoride. They have significantly lower evaporation temperatures, as is apparent from the table below (q represents quinolate):

| Material | Evaporation Temparature/° C. | Vacuum Pressure/Pa | Evaporation Rate/Å s$^{-1}$ |
|---|---|---|---|
| Liq | 320 | $\leq 5 \times 10^{-5}$ | 1.0 |
| LiF | 580 | $\leq 5 \times 10^{-5}$ | 0.1 |

Suitable metal quinolates include the alkali metal quinolates and the alkaline earth quinolates. Preferred metal quinolates have the formula

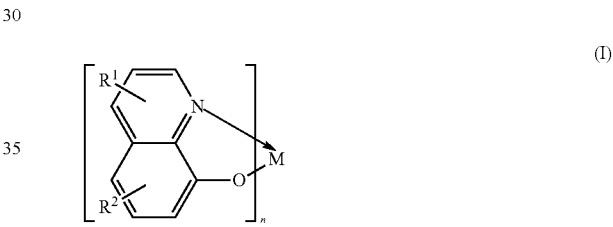

(I)

wherein M is a metal; n is the valence state of M when complexed with quinolate; and $R^1$ and $R^2$ which may be the same or different are selected from $C_1$-$C_4$ alkyl and substituted or unsubstituted monocyclic or polycyclic aryl or heteroaryl, aralk-($C_1$-$C_4$)-yl or aryloxy. Lithium quinolate and lithium 2-methylquinolate are preferred compounds and are preferably the result of reaction between a lithium alkyl or alkoxide with substituted or unsubstituted 8-hydroxy quinoline in a solvent which comprises acetonitrile. Lithium quinolates made as described above are of high purity and readily sublimable.

The electron injection layer deposited direct onto the cathode may alternatively comprise a compound of the formula

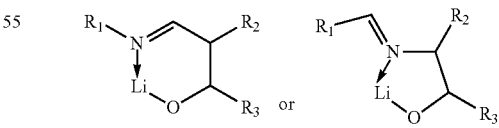

wherein $R_1$ is a 1-5 ring aryl (including polycyclic aryl or aryl-substituted polycyclic aryl), aralkyl or heteroaryl group which may be substituted with one or more $C_1$-$C_4$ alkyl or alkoxy substituents; and $R_2$ and $R_3$ together form a 1-5 ring aryl (including polycyclic or aryl-substituted polycyclic aryl), aralkyl or heteroaryl group which may be substituted with one or more $C_1$-$C_4$ alkyl or alkoxy substituents. A compound of the above formula may be used alone or in combination with another electron injection material e.g. a quinolate such as lithium or zirconium quinolate. The Schiff base preferably comprises at least 30 wt % of the electron injection layer, more preferably at least 50 wt %.

In the formula set out above, $R_1$ may be polycyclic aryl e.g. naphthyl, anthracenyl, tetracenyl, pentacenyl or a perylene or pyrene compound or may have up to aromatic rings arranged in a chain e.g. biphenyl. It is preferably phenyl or substituted phenyl. $R_2$ and $R_3$ together may form the same groups as $R_1$ and are preferably phenyl or substituted phenyl. Where substituents are present they may be methyl, ethyl, propyl or butyl, including t-butyl substituted, or may be methoxy, ethoxy, propoxy or butoxy including t-butoxy substituted. Particular compounds include

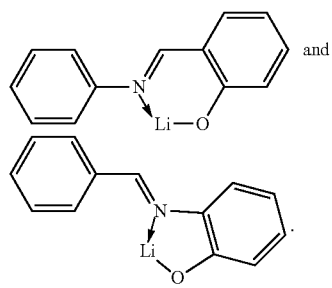

Lithium compounds whose formulae are set out above are believed from MS measurements to be capable of forming cluster compounds or oligomers in which 2-8 molecules of formula as set out above are associated e.g. in the form of trimeric, tetrameric, hexameric or octomeric oligomers. It is believed that such lithium compounds may in some embodiments associate in trimeric units having a core structure which has alternating Li and O atoms in a 6-membered ring, and that these trimeric units may further associate in pairs. The existence of such structures in lithium quinolate has been detected by crystallography, see Begley et al., Hexakis(μ-quinolin-8-olato)hexylithium (I): a centrosymmetric doubly stacked trimer, *Acta Cryst.* (2006), E62, m1200-m1202, the disclosure of which is incorporated herein by reference. It is also believed that formation of oligomeric structures of this type imparts a greater covalent character to the Li—O bonds which may be responsible for the volatility of many of the compounds of the invention which enables them to be deposited at relatively low temperatures by vacuum sublimation. However, other structures may also be possible e.g. cubic structures.

Cathode

The cathode on which there is the layer of electron injection material is in some embodiments a low work function metal. The metal electrode may consist of a plurality of metal layers; for example a higher work function metal such as aluminium deposited on the substrate and a lower work function metal such as calcium deposited on the higher work function metal. The work function of some metals are listed below in Table 1

TABLE 1

| Metal | Work Function eV* |
|-------|-------------------|
| Li    | 2.9               |
| Na    | 2.4               |
| K     | 2.3               |
| Cs    | 1.9               |
| Ba    | 2.5               |
| Ca    | 2.9               |
| Nb    | 2.3               |
| Zr    | 4.05              |
| Mg    | 3.66              |
| Al    | 4.2               |
| Cu    | 4.6               |
| Ag    | 4.64              |
| Zn    | 3.6               |
| Sc    | 3.5               |

*Handbook of Chemistry and Physics

In many embodiments, aluminium is used as the cathode either on its own or alloyed with elements such as magnesium or silver, although in some embodiments other cathode materials e.g. calcium may be employed. In an embodiment the cathode may comprise a first layer of alloy e.g. Li—Ag, Mg—Ag or Al—Mg closer to the electron injection or electron transport layer and a second layer of pure aluminium further from the electron injection or electron transport layer. Cathode materials may also be on transparent plate materials which may be of glass or may be of plastics which may be rigid or flexible and may be optically transparent As regards plastics substrates, rigid or flexible transparent plastics materials may be used, preferably materials which are dimensionally stable, impermeable to water (including water vapour) of relatively high Tg. PEN is a preferred material, other materials that may be used including PES, PEEK and PET. The plastics may be coated with a conductive film and may also have a barrier coating to improve resistance to moisture which may be encountered under working conditions e.g. atmospheric moisture.

How the invention may be put into effect will now be described with reference to the following examples.

Preparative Methods

Synthesis of A-ST 1,4-[Bis(2,2'-quinolinyl)vinyl)]benzene

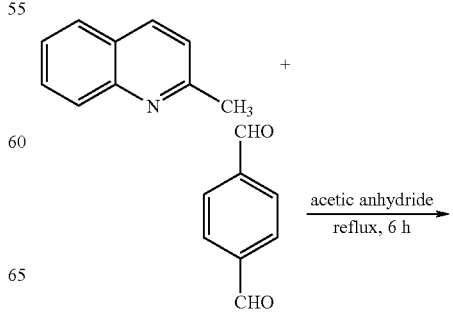

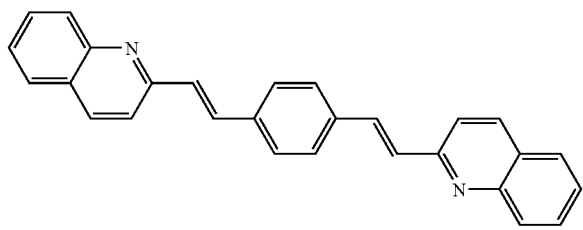 [SMILES: C(=C\c1ccc2ccccc2n1)/c1ccc(/C=C/c2ccc3ccccc3n2)cc1]

A mixture of 2-methylquinoline (quinaldine, 46.8 g; 0.35 mole) and benzene-1,4-dicarboxaldehyde (25.0 g; 0.1745 mole) was refluxed in acetic anhydride (70 ml) for 6 hours. The reaction mixture was allowed to cool, overnight. Methanol was added to the reaction mixture and the product was filtered off under suction. The filter cake was washed thoroughly with de-ionised water, followed by methanol. The deep yellow crystalline solid was dried under vacuum at 80° C. for 8 hours. Yield quantitative. Mp 246° C. (DSC, onset). The product was sublimed purified.

Synthesis of A-Ph-ST (a) 2-Methyl-6-phenylquinoline

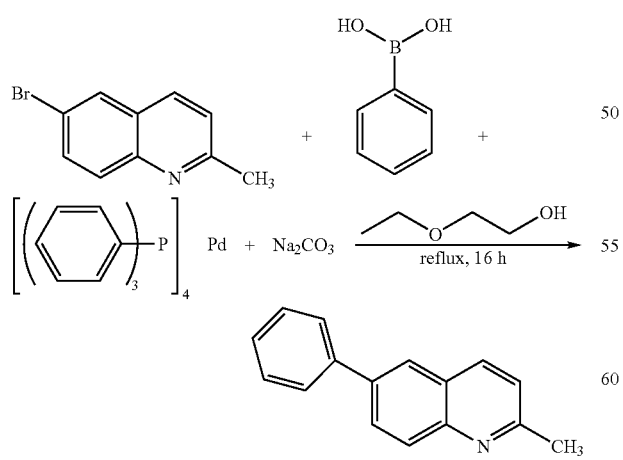

2-Methyl-6-phenylquinoline was prepared from 6-Bromo-2-methylquinoline by Suzuki coupling with phenylboronic acid and tetrakis(triphenylphosphine) palladium(0) in refluxing 2-ethoxyethanol. To a solution 6-Bromo-2-methylquinoline (8.9 g; 40 mmol) in 2-ethoxyethanol (100 ml) was added tetrakis(triphenylphosphine) palladium (1 g; 0.86 mmol) and the reaction mixture was stirred at room temperature for 10 minutes. Phenylboronic acid (5 g; 41 mmol) in ethoxyethanol (50 ml) was then added followed by aqueous sodium carbonate (8.4 g; 79 mmol) in water (50 ml). The reaction mixture was magnetically stirred and refluxed for 16 h. The cooled reaction mixture was extracted with chloroform (3×100 ml), washed with brine, dried over anhydrous magnesium sulphate and solvent concentrated. The residue with the solvent was filtered through a silica gel column and the colourless solution was evaporated. The residue was triturated with petroleum spirit (30-40° C.) and recrystallised from ether to give an off white solid, 5.5 g (63%); Mp 95° C. (DSC, onset). Elemental analysis: Found C, 87.60; H, 5.98; N, 6.32; $C_{16}H_{13}N$ requires C, 87.64; H, 5.98; and N, 6.39%.

(b) 1,4-[Bis(6,6'-phenyl-2,2'quinolin-2-yl)vinyl)]benzene

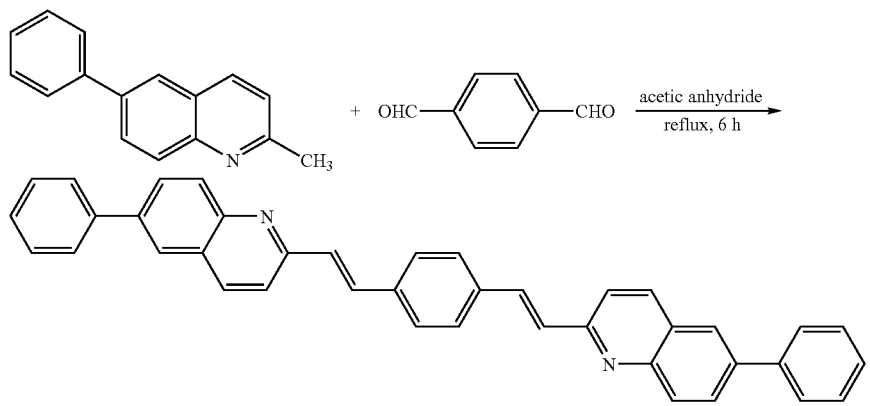

A mixture of 2-methyl-6-phenylquinoline (5.2 g; 24 mmol) and benzene-1,4-dicarboxaldehyde (1.6 g; 12 mmol in acetic anhydride (20 ml) was refluxed under nitrogen atmosphere for 6 hours. To the cooled reaction mixture methanol (50 ml) and water (10 ml) was added and the shiny yellowish solid was filtered off, washed well with methanol, water and finally with diethyl ether. The product dried under vacuum at 80° C. Yield 4.6 g (72%). Mp 312° C. (DSC, onset). The product was further purified by sublimation.

Synthesis of A-BP-ST (a) 6-Biphenyl-2-methylquinoline

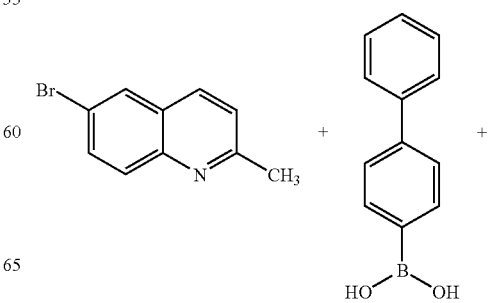

-continued

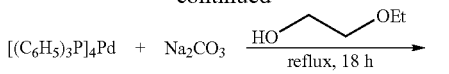
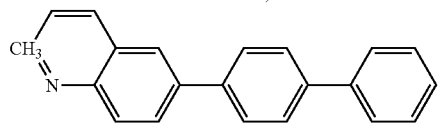

To a solution 6-bromo-2-methylquinoline (5.0 g; 22.5 mmol) in 2-ethoxyethanol (80 ml) was added tetrakis(triphenylphosphine) palladium (1 g; 0.86 mmol) and the reaction mixture was stirred at room temperature under nitrogen atmosphere for 10 minutes. 4-Biphenylboronic acid (4.7 g; 23.7 mmol) was added followed by ethoxyethanol (20 ml). Then an aqueous solution of sodium carbonate (10 g; 94 mmol) in water (50 ml) was added. The reaction mixture was magnetically stirred and refluxed under nitrogen for 18 h. The cooled reaction mixture was extracted with chloroform (3×100 ml), washed with brine, dried over anhydrous magnesium sulphate and solvent concentrated. The solution was filtered through a silica gel column and the solvent evaporated. The residue was triturated with petroleum spirit (30-40° C.) and ether to give an off white solid, 4.1 g (62%); The product was recrystallised from chloroform-methanol to give a colourless solid showing violet fluorescence under UV lamp. Mp 206° C. (DSC, onset). Elemental analysis: Found C, 89.35; H, 5.82; N, 4.78; $C_{22}H_{17}N$ requires C, 89.65; H, 5.37; and N, 4.98%.

(b) 1,4-[Bis(6,6'-biphenyl-2,2'quinolin-2-yl)vinyl)]benzene

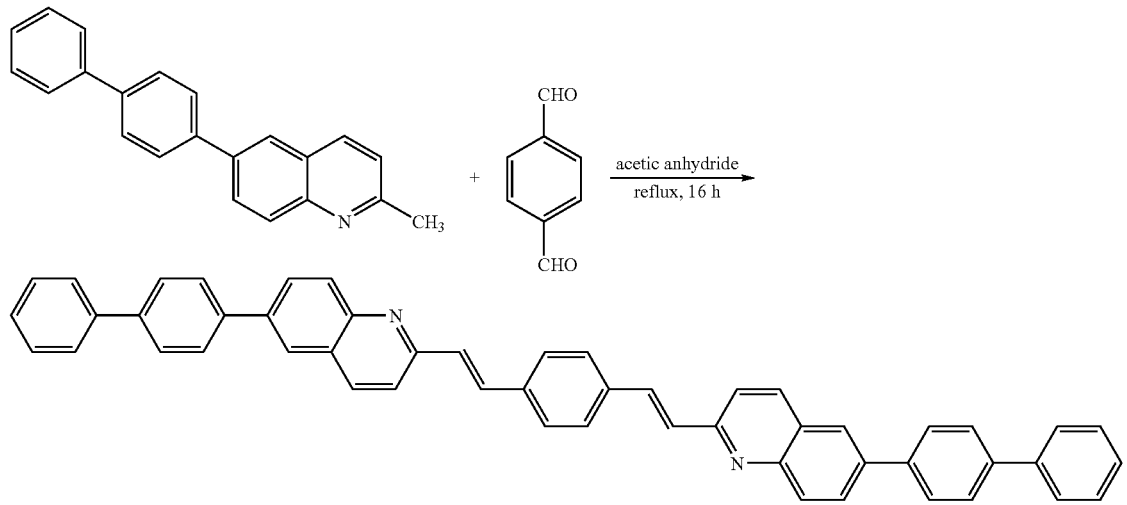

A mixture of 6-biphenyl-2-methylquinoline (3.0 g; 0.010 mole) and benzene-1,4-dicarboxaldehyde (0.7; 0.005 mole) was refluxed in acetic anhydride (25 ml) for 16 hours. The solid separated out on cooling was isolated after addition of methanol. The product was filtered off, washed with water, methanol and finally with diethyl ether. Yield 3.2 g; (91%). The product was sublimed purified. Mp 256° C. (DSC, onset), a small hump appeared on the DSC around 355° C.

Synthesis of A-DF-ST (a) 6-(2',4'-Difluorophenyl)-2-methylquinoline

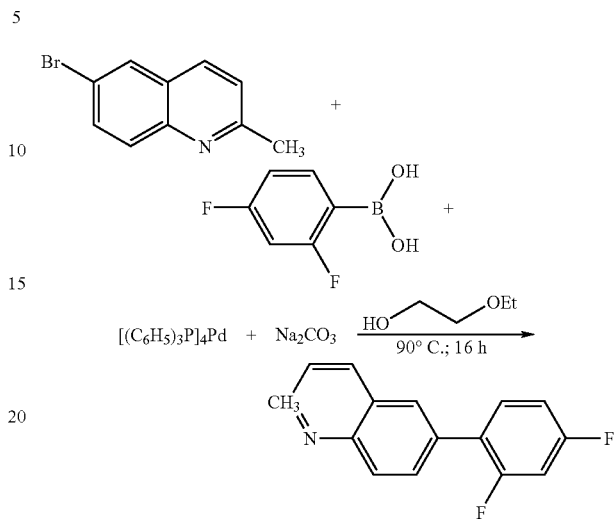

To a solution 6-Bromo-2-methylquinoline (4.7 g; 0.021 mol) in 2-ethoxyethanol (80 ml) was added tetrakis(triphenylphosphine) palladium (0.5 g; 0.0004 mol) and the reaction mixture was stirred at room temperature under nitrogen atmosphere for 5 minutes. 2,4-Difluorophenylboronic acid (3.5 g; 0.022 mol) was added followed by ethoxyethanol (20 ml). Sodium carbonate (10 g; 0.094 mol) in water (50 ml) was added and the reaction mixture was magnetically stirred and heated under nitrogen at 90° C. for 16 h. The cooled reaction mixture was filtered through a pad of Celite, hyflo supercel and then extracted with dichloromethane (3×100 ml), after addition of de-ionised water. The organic layer was washed with brine, dried over anhydrous magnesium sulphate and solvent removed to give the residue, which was triturated with ether and cooling in the refrigerator gave a solid. This was filtered off and dried under vacuum at 60° C. to give a colourless solid. Yield 3.9 g (72%). Mp 86° C. (DSC, onset). Elemental analysis: Found C, 73.76; H, 4.39; N, 5.38; $C_{16}H_{11}NF_2$ requires C, 75.28; H, 4.34; and N, 5.49%.

(b) 1,4-[Bis(6,6'-(2,4-difluorophenyl)-2,2'quinolin-2-yl)vinyl)]benzene

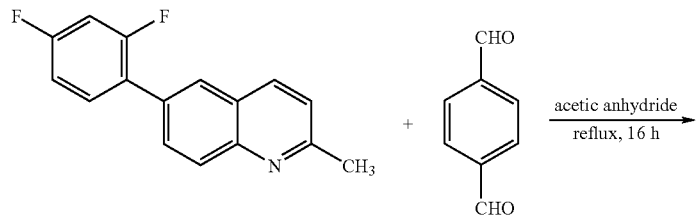

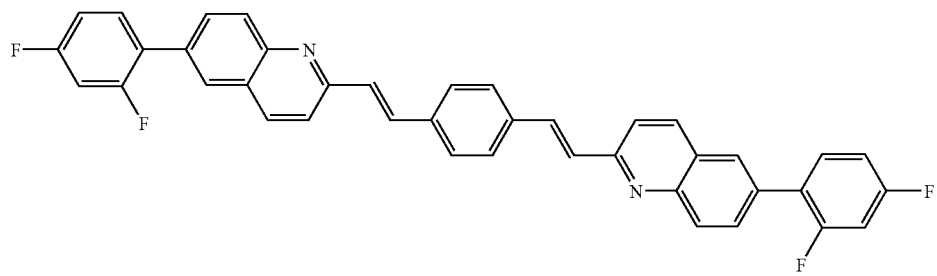

A mixture of 6-(2',4'-Difluorophenyl)-2-methylquinoline (3.5 g; 0.014 mole) and benzene-1,4-dicarboxaldehyde (0.95; 0.00685 mole) was refluxed in acetic anhydride (35 ml) for 18 h. The reaction mixture was allowed to cool to room temperature and methanol (50 ml) was added. The solid that separated out was filtered off, washed with methanol, de-ionised water and diethyl ether. The product was dried under vacuum at 75° C., Yield 3.2 g; (76%). Mp 268° C. (DSC, onset). The product sublimed purified twice.

Synthesis of A-Np-ST (a) 6-(1-Naphthyl)-2-methyl quinoline

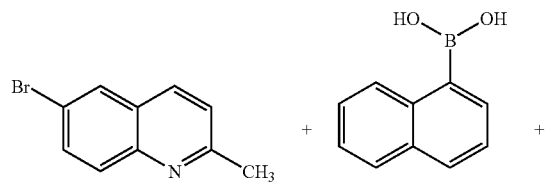

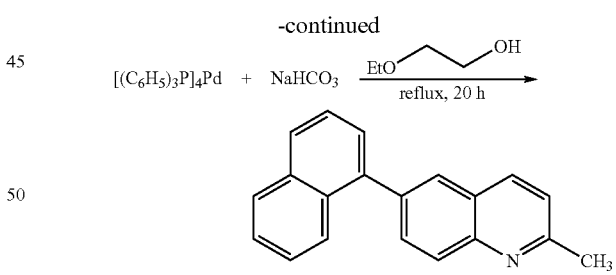

6-Bromo-2-methylquinoline (32.5; 0.145 mole) was dissolved in 2-ethoxy ethanol (200 ml) and to the magnetically stirred solution under nitrogen was added tetrakis(triphenyl phosphine) palladium (5.1 g; 0.0044 mole) followed by 2-ethoxy ethanol (25 ml). After 5 minutes stirring at room temperature 1-naphthaleneboronic acid (25.0 g; 0.145 mole) was added followed by 2-ethoxyethanol (75 ml). Sodium hydrogencarbonate (35 g; 0.42 mole) in water (200 ml) was added all at once and the reaction mixture was stirred and heated under nitrogen atmosphere at 90° C. for 20 h. After 1 h, the reaction mixture became orange in colour. The reaction mixture was allowed to cool, dichloromethane (100 ml) was added and the reaction mixture was filtered off under suction using celite, with a layer of silica gel on the top. To the filtrate further dichloromethane (250 ml) was added, extracted with de-ionised water (2×300 ml) and finally with brine (250 ml). The organic phase was dried over anhydrous magnesium sulphate and the solvent removed to give a thick liquid. Trituration with diethyl ether and cooling in the refrigerator gave a light yellow solid. The product was dried under vacuum at 80° C., (22 g; 56%). Mp 111° C. (DSC, onset). Elemental analysis: Found C, 89.16; H, 5.58; N, 5.15; $C_{20}H_{15}N$ requires C, 89.19; H, 5.61; and N, 5.20%.

(b) 1,4-[Bis(6,6'-naphthyl-2,2'quinolin-2-yl)vinyl)]benzene

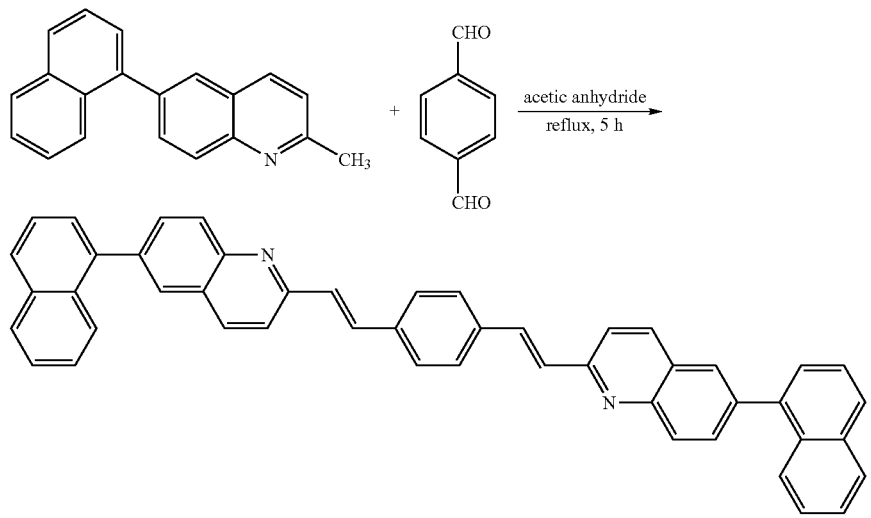

A mixture of 6-naphthyl-2-methylquinoline (11 g; 0.041 mole) and benzene-1,4-dicarboxaldehyde (2.75 g; 0.02 mole) was refluxed in acetic anhydride (30 ml) for 6 h. During this time a yellow solid separated out from the reaction mixture. To the cooled reaction mixture methanol (50 ml) was added and the product filtered off under suction. The filter cake was washed with de-ionised water and then with methanol to remove any traces of acetic anhydride. The product dried under vacuum at 80° C., yield 9.5 g (73%). Mp 276° C. (DSC, onset). The product further purified by sublimation.

Synthesis of A-PyR-ST (a) 6-Pyrenyl-2-methylquinoline

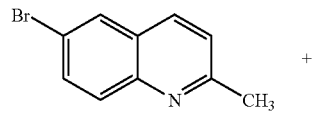

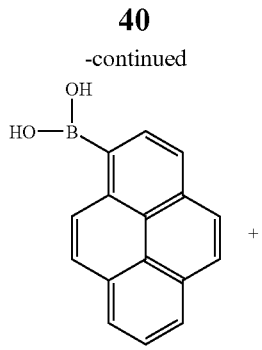

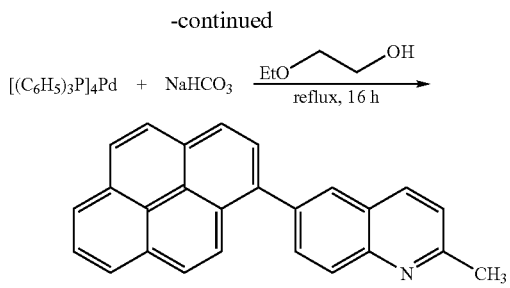

6-Bromo-2-methylquinoline (4.5; 20 mmole) was dissolved in 2-ethoxy ethanol (30 ml) and to the magnetically stirred solution under nitrogen was added tetrakis(triphenyl phosphine) palladium (1 g; 0.9 mmole). After 5 minutes stirring at room temperature, 1-pyreneboronic acid (5.0 g; 20 mmole) was added followed by 2-ethoxyethanol (10 ml). Sodium hydrogencarbonate (10 g; 94 mmole) in water (60 ml) was added all at once and the reaction mixture was stirred and heated under nitrogen atmosphere at 90° C. for 18 h. The reaction mixture was allowed to cool, dichloromethane (100 ml) was added and the reaction mixture was filtered through a layer of silica gel. To the filtrate further dichloromethane (50 ml) was added and extracted with de-ionised water (2×100 ml). The organic phase was dried over anhydrous magnesium sulphate and the solvent removed to give the required product. The product was dried under vacuum at 80° C., Yield 4.5 g (67%). Mp 133° C. (DSC, onset). Elemental analysis: Found C, 90.80; H, 5.09; N, 4.32; $C_{26}H_{17}N$ requires C, 90.93; H, 4.99; and N, 4.08%.

(b) 1,4-[Bis(6,6'-pyrenyl-2,2'quinolin-2-yl)vinyl)]benzene

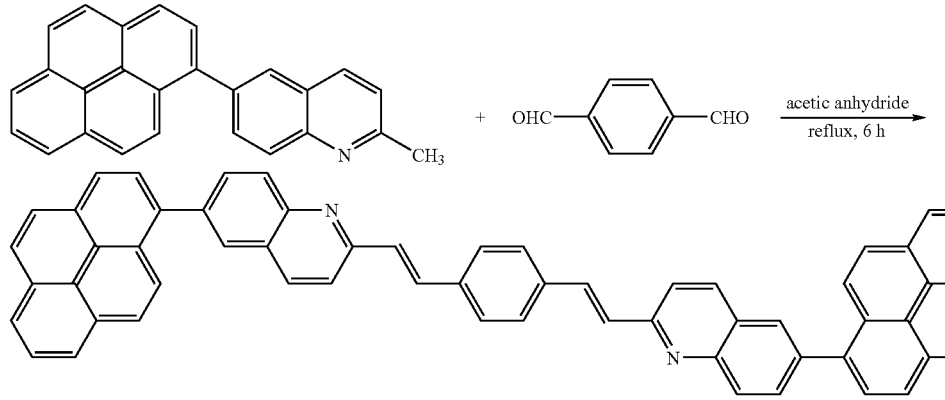

A mixture of 6-pyrenyl-2-methylquinoline (3.0 g; 9.1 mmole) and benzene-1,4-dicarboxaldehyde (0.61 g; 4.5 mmol) was refluxed in acetic anhydride (20 ml) for 18 h and allowed to cool to room temperature. Methanol (25 ml) was added to the yellowish green reaction mixture and the product filtered off under suction. The filter cake was washed thoroughly with methanol, de-ionised water, diethyl ether and finally with methanol. The product dried under vacuum at 80° C. Yield 2.9 g (83%). The product further purified by sublimation. Mp 266° C. (DSC, onset), 282 (DSC, peak).

Synthesis of A-QOx-ST 1,4-[Bis(2,2-quinoxalin-2-yl)vinyl)]benzene

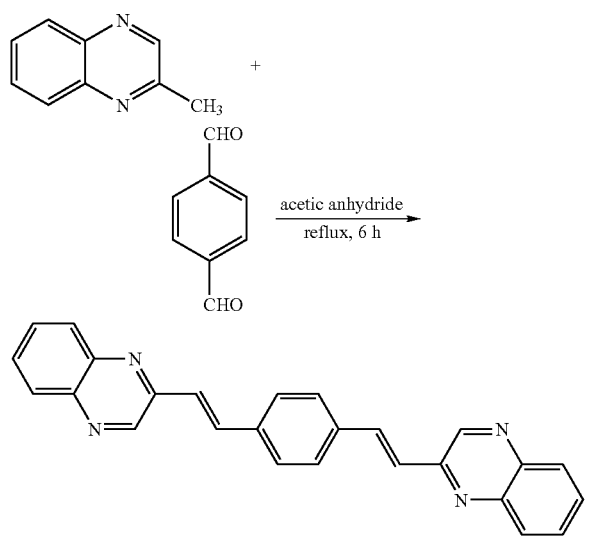

A mixture of 2-methylquinoxaline (10 g; 0.0693 mole) and benzene-1,4-dicarboxaldehyde (4.65 g; 0.035 mole) was refluxed in acetic anhydride (30 ml) for 6 h, and the reaction mixture was allowed to cool to room temperature. Excess methanol and small amounts of water was added to the reaction mixture and the red-brown solid that separated out was filtered off, washed thoroughly with methanol and dried under vacuum at 80° C. Yield 6.2 g (46%). The product was purified by sublimation. Mp 266° C.

Synthesis of A-Th-ST

(a) 2-methyl-6-(2-thienyl)quinoline

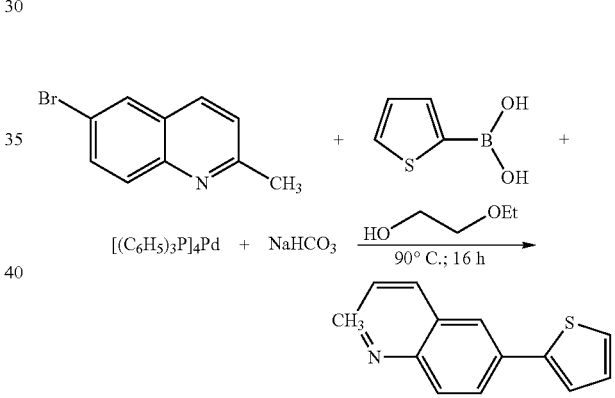

To a solution 6-Bromo-2-methylquinoline (17.4 g; 0.078 mol) in 2-ethoxyethanol (100 ml) was added tetrakis(triphenylphosphine) palladium (2.7 g; 0.0023 mol) and the reaction mixture was stirred at room temperature under nitrogen atmosphere for 5 minutes. 2-Thienylboronic acid (10.0 g; 0.078 mol) was added followed by ethoxyethanol (70 ml). Sodium hydrogencarbonate (20 g; 0.24 mol) in water (100 ml) was added and the reaction mixture was magnetically stirred and heated under nitrogen at 90° C. for 16 h. The cooled reaction mixture was filtered through a pad of Celite hyflo supercel and then extracted with dichloromethane (2×150 ml), after addition of de-ionised water. The organic layer was washed with brine, dried over anhydrous magnesium sulphate and solvent removed to give a light brown liquid. The liquid was distilled under reduced pressure to remove ethoxy ethanol. The residue was triturated with diethyl ether and cooled in the refrigerator to give an off white solid, 10.6 g (61%); Mp 87° C. (DSC, onset). Elemental analysis: Found C, 74.72; H 4.92; N, 6.12; S 13.43; $C_{14}H_{11}NS$ requires C, 74.63; H 4.92; N, 6.21; and S, 14.24%.

(b) 1,4-[Bis(6,6'-(2-thienyl)-2,2'quinolin-2-yl)vinyl)]benzene

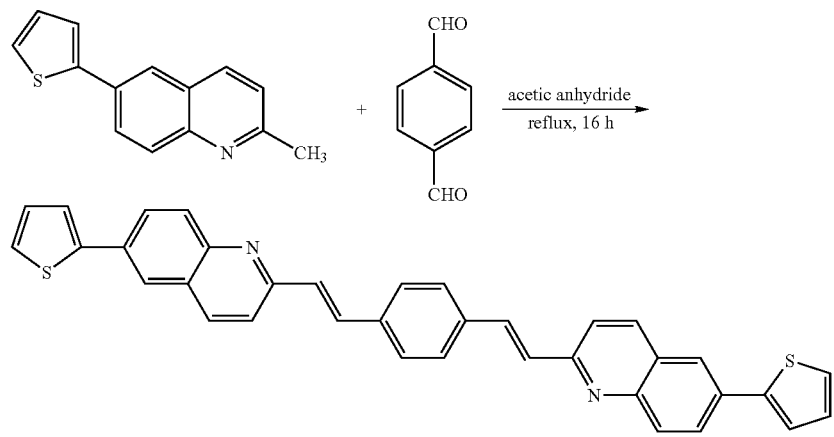

A mixture of 2-methyl-6-(2-thienyl)quinoline (10.25 g; 0.046 mole) and benzene-1,4-dicarboxaldehyde (3.1; 0.023 mole) was refluxed in acetic anhydride (35 ml) for 18 h. The reaction mixture was allowed to cool to room temperature and methanol (50 ml) was added. A yellow-green solid separated out. The solid was filtered off under suction and the filter cake was washed thoroughly with methanol, de-ionised water and finally with methanol and diethyl ether. The product dried under vacuum at 75° C., Yield 9.5 g; (76%). Mp 330° C. (DSC, onset). The product sublimed purified.

Properties of the above mentioned compounds are set out in the following Table.

| Compound | Structure | EA (%) Theory | EA (%) Found | M.Pt. DSC Peak (°C) | Tg (°C) | FL. $\lambda_{max}$ (nm) Solution |
|---|---|---|---|---|---|---|
| A-ST | 2,2'-Bis (vinylquinolinyl)-1,4-benzene | C = 87.47<br>H = 5.24<br>N = 7.29 | C = 87.57<br>H = 5.18<br>N = 7.37 | 246 | No Tg | 439 |
| A-Ph-ST | 6,6-Bis(phenyl-2,2-vinylquinolinyl) benzene | C = 89.52<br>H = 5.26<br>N = 5.22 | C = 89.46<br>H = 5.25<br>N = 5.22 | 312 | No Tg | 429 |
| A-Bp-ST | 6,6-Bis(biphenyl-2,2-vinylquinolinyl) benzene | C = 90.67<br>H = 5.27<br>N = 4.07 | C = 90.28<br>H = 5.44<br>N = 3.80 | 254 | ~180 | To be determined |

| | | | |
|---|---|---|---|
| A-DF-ST | C = 78.94<br>H = 3.98<br>N = 4.60 | C = 78.19<br>H = 3.93<br>N = 4.40 | 268 | No Tg | 427 |

6,6-Bis(2,4-fluorophenyl-2,2-vinylquinolinyl)benzene

| | | | |
|---|---|---|---|
| A-Np-ST | C = 90.54<br>H = 5.07<br>N = 4.40 | C = 89.81<br>H = 5.12<br>N = 4.24 | 276 | 94 | 430 |

6,6-Bis(napthyl-2,2-vinylquinolinyl)benzene

| | | | |
|---|---|---|---|
| A-PyR-ST | C = 91.81<br>H = 4.62<br>N = 3.57 | C = 91.55<br>H = 4.89<br>N = 3.44 | 266 | 88 | 438 |

6,6-Bis (1,1'-pyrenyl-2,2'-vinylquinolinyl) benzene

-continued
| | | | | |
|---|---|---|---|---|
| A-QOx-ST 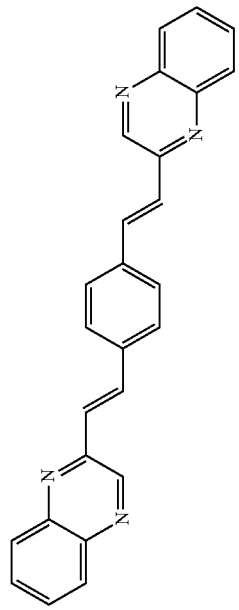 1,4-[Bis(2,2-quinoxalin-2-yl)vinyl)] benzene | C 80.81<br>H 4.70<br>N 14.50 | C 81.45<br>H 4.74<br>N 14.69 | 266 | No Tg | 441 |
| A-Th-ST 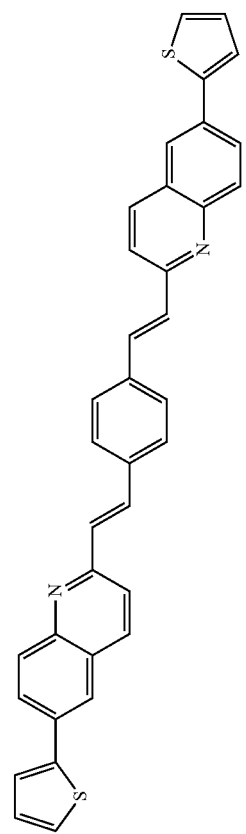 4-[Bis(6,6'-(2-thienyl)-2,2'quinolin-2-yl)vinyl)] benzene | C 78.80<br>H 4.41<br>N 5.10<br>S 11.69 | C 78.68<br>H 4.49<br>N 4.93<br>S 11.61 | 330 | No Tg | 437 and 460 (sh) |

Device Structure

A pre-etched ITO coated glass piece (10×10 cm$^2$) was used. The device was fabricated by sequentially forming layers on the ITO, by vacuum evaporation using a Solciet Machine, ULVAC Ltd. Chigacki, Japan. The active area of each pixel was 3 mm by 3 mm. The coated electrodes were encapsulated in an inert atmosphere (nitrogen) with UV-curable adhesive using a glass back plate. Electroluminescence studies were performed with the ITO electrode was always connected to the positive terminal. The current density vs. voltage studies were carried out on a computer controlled Keithly 2400 source meter.

EXAMPLE 1

Figure 2:
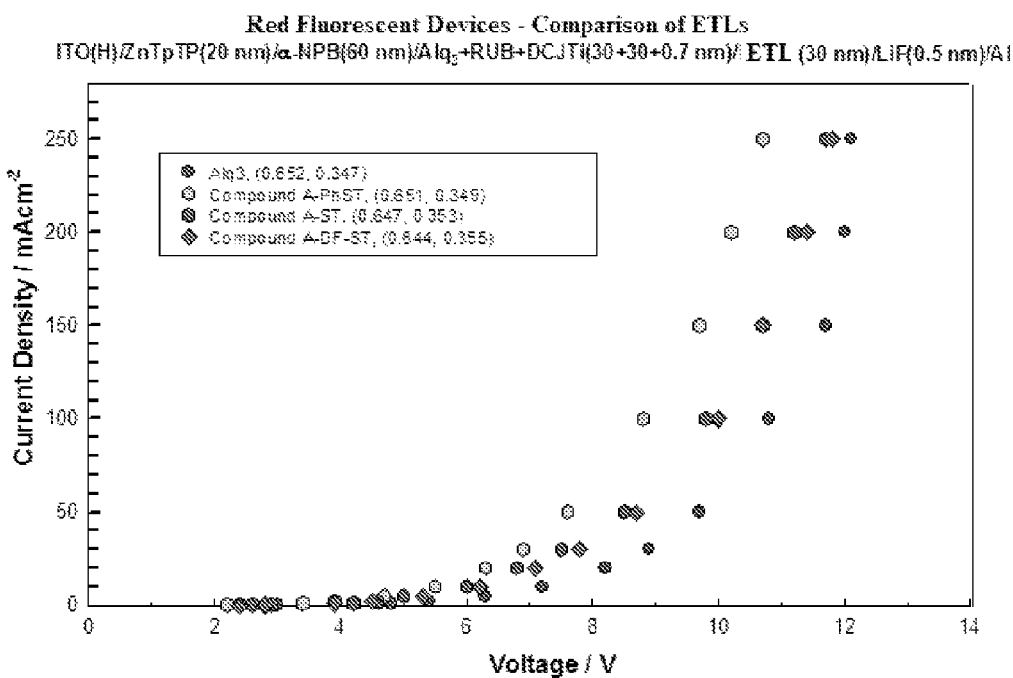

Devices with green and red emission were formed by the method described above consisting of an anode layer, buffer layer, hole transport layer, electroluminescent layer (doped material), electron transport layer, electron injection layer and cathode layer, the layer composition being as indicated in FIGS. 1 and 2 and film thicknesses being in nm. The CIE colour coordinates and the current density-voltage characteristics were as shown in FIGS. 1 and 2.

Performance of devices was further evaluated with the following results for various test compounds

| Material | Mobility/ Cm$^2$V$^{-1}$s$^{-1}$ | Tg ° C. | Tg ° C. | $V_{on}$/V(AlQ$_3$) at 1000 cdm$^{-2}$ | Lifetime $T_{1/2}/T_{1/2}$ (Alq$_3$) |
|---|---|---|---|---|---|
| Alq$_3$ | 2 × 10$^{-6}$ | 175 | 414 | 1 | 1 |
| Zrq$_4$ | 1 × 10$^{-5}$ | No Tg | 388 | 0.8 | 3 |
| BPhen | 5 × 10$^{-5}$ | 71 | 220 | 0.7 | 0.02 |
| A-St | 6 × 10$^{-5}$ | No Tg | 246 | 0.8 | 3.5 |
| A-Bp-St | 6 × 10$^{-5}$ | 180 | 254 | 0.8 | 3.5 |

In the above table, BPhen is 4,7-diphenyl-1,9-phenanthroline.

The invention claimed is:

1. A composition comprising a compound of the formula $R^1(CR^3{=}CR^4)_nAr(CR^4{=}CR^3)_nR^2$ wherein:
    n is 0 or 1;
    Ar represents aryl or heteroaryl having 1-5 aromatic rings which is optionally chain or fused or a combination of chain and fused, which is optionally substituted with alkoxy, fluoro, fluoroalkyl or cyano and which in the case of a 5-membered ring nitrogen heteroatom is optionally N-substituted with aryl or substituted aryl optionally further substituted with alkoxy, fluoro, fluoroalkyl or cyano;
    R$^1$ and R$^2$ independently represent aryl or nitrogen, oxygen or sulphur-containing heteroaryl having two to four fused aromatic rings one of which is optionally a 5-membered and optionally substituted by aryl or heteroaryl having 1-5 chain or fused aromatic rings which is optionally further substituted with alkoxy, fluoro, fluoroalkyl or cyano; and
    R$^3$ and R$^4$ independently represent hydrogen, methyl, ethyl or benzyl, and a dopant.

2. The composition as claimed in claim 1, having at least one of the following features:
    (i) n is 1;
    (ii) Ar represents phenyl or naphthyl optionally substituted with fluoro, fluoroalkyl or cyano;
    (iii) Ar represents a residue of benzene-1,4-dicarboxaldehyde;
    (iv) Ar represents a residue of benzene-1,2-dicarboxaldehyde, benzene-1,3-dicarboxaldehyde, naphthalene 1,2-dicarbaldehyde, naphthalene-1,4-dicarbaldehyde, naphthalene 2,6-dicarbaldehyde, naphthalene-1,8-dicarbaldehyde, anthracene-1,4-dicarbaldehyde, anthracene-2,3-dicarbaldehyde, anthracene-4,9-dicarbaldehyde, anthracene-9,10-dicarbaldehyde or biphenyl-4,4'-dicarboxaldehyde;
    (v) R$^1$ and R$^2$ independently represent bicyclic heteroaryl having 1, 2 or 3 ring nitrogen atoms;
    (vi) R$^1$ and R$^2$ represent quinolinyl which may be unsubstituted or substituted with aryl or heteroaryl which is monocyclic or which may have two aryl or heteroaryl rings which may be chain or fused and which may be further substituted with alkoxy, fluoro, trifluoromethyl, cyano or thiophenyl;
    (vii) R$^1$ and R$^2$ independently represent imidazole, oxazole or thiazole which in the case of imidazole may be substituted on nitrogen by aryl or heteroaryl; and
    (viii) R$^1$ and/or R$^2$ is methyl.

3. The composition as claimed in claim 1, wherein the compound is of formula:

$R^1(CH{=}CH)_nAr(CH{=}CH)_nR^2$ wherein n, R$^1$, R$^2$ and Ar are as defined in claim 1.

4. The composition according to claim 1, wherein the compound is of formula

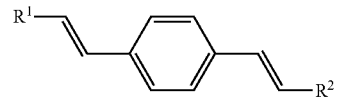

wherein R$^1$ and R$^2$ are as defined in claim 1.

5. The composition according to claim 1, wherein the compound is selected from the group consisting of:
    2,2'-bis (vinylquinolinyl)-1,4- benzene;
    6,6-bis(phenyl-2,2-vinylquinolinyl) benzene;
    6,6-Bis(biphenyl-2,2-vinylquinolinyl) benzene
    6,6-bis(2,4-fluorophenyl-2,2-vinylquinolinyl)benzene;
    6,6-bis(napthyl-2,2-vinylquinolinyl) benzene
    6,6'-bis(1,1'-pyreny-2,2'-vinylquinolinyl)benzene;
    1,4-[Bis(2,2-quinoxalin-2-yl)vinyl)]benzene; and
    4-[bis(6,6'-(2-thienyl)-2,2'quinolin-2-yl)vinyl)]benzene.

6. The composition of claim 1, which further comprises a second host or electron transport material.

7. The composition of claim 6, having at least one of the following features:
    (i) the compound according to claim 1 comprises at least 50 wt % of the composition;
    (ii) the second host or electron transport material comprises a small molecule;
    (iii) the second host or electron transport material comprises a metal quinolate or a substituted metal quinolate;
    (iv) the second host or electron transport material comprises a phenanthroline compound;
    (v) the second host or electron transport material comprises bathophen or 4,7-diphenyl- 1,10-phenanthroline;
    (vi) the second host or electron transport material comprises a compound of formula $[Ar](CH{=}CH{-}R_1)_n$ wherein n is an integer from 1 to 4; [Ar] is a polycyclic aromatic or heteroaromatic scaffold optionally substituted with one or more alkyl or alkoxy groups; and $R_1$ is a 5-membered heteroaryl group optionally substituted with methyl, aryl or heteroaryl, or is phenyl or naphthyl optionally substituted with methyl, methoxy, trifluoromethyl or cyano or is biphenyl or is substituted biphenyl; and (vii) the second host or electron transport material comprises any of 2,9-bis(4,4'-trifluoromethyl styrenyl)phenenthroline, 2,9-bis((E)-2-(5-(thiophen-2-yl)thiophen-2-yl)vinyl)-1,10-phenanthroline, 2,9-bis(4,4'-cyanostyrenyl) phenanthroline and 2,9-bis(2,2'-vinyl-5,5'-phenyl thiophenyl) phenanthroline.

8. The composition of claim 6, wherein the second host, electron transport material or dopant is any of:

(i) a nitrogen-containing aromatic compound in an amount effective to increase electron transport;

(ii) a nitrogen-containing sublimable small molecule of any of the formulae (a) to (g) below in an amount effective to increase electron transport:

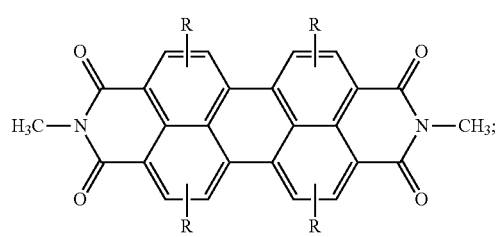

(a)

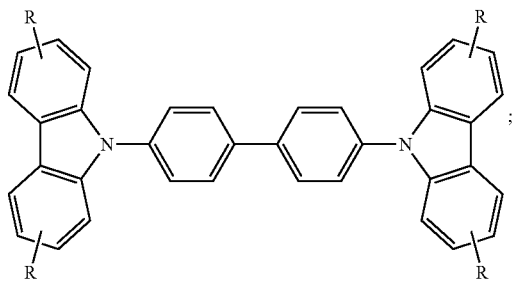

(b)

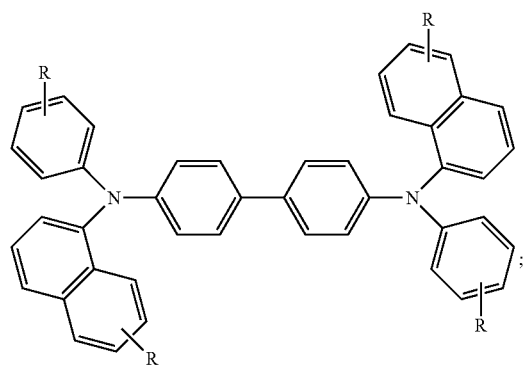

(c)

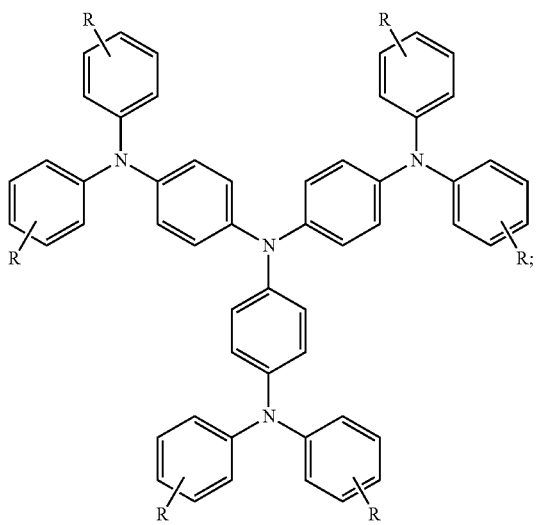

(d)

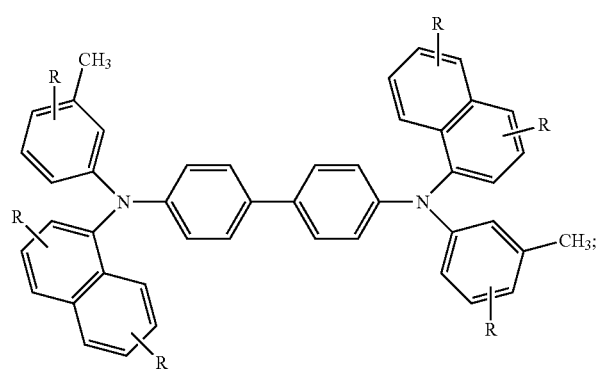

(e)

-continued

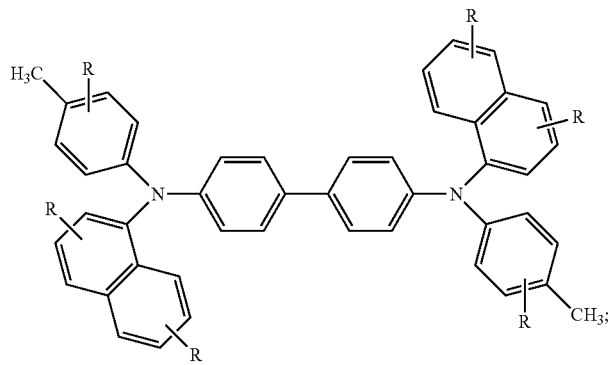
(f)

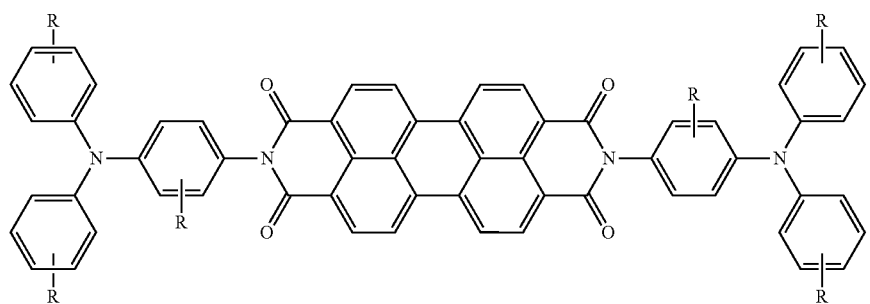
(g)

wherein the groups R in any of the formulae in (a) to (g) can be the same or different and are selected from hydrogen; substituted and unsubstituted aliphatic groups; substituted and unsubstituted aromatic, heterocyclic and polycyclic ring structures; halogens; and thiophenyl groups; and wherein in formula (a) the methyl groups may be replaced by $C_1$-$C_4$ alkyl or monocyclic or polyclic aryl or heteroraryl which may be further substituted e.g. with alkyl, aryl or arylamino;

(iii) any of the following compounds in an amount effective to promote electron transport:

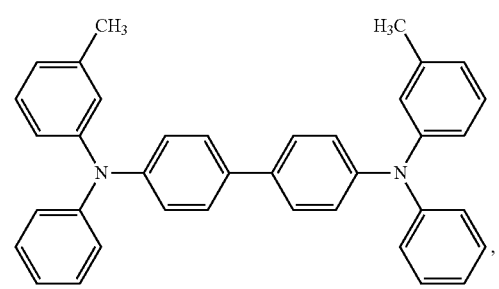,

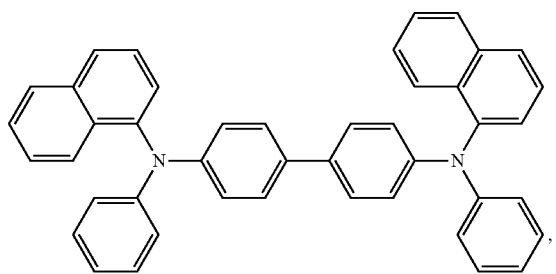,

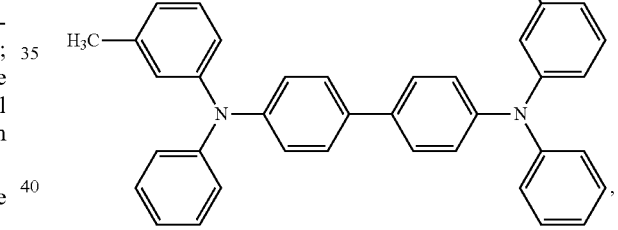,

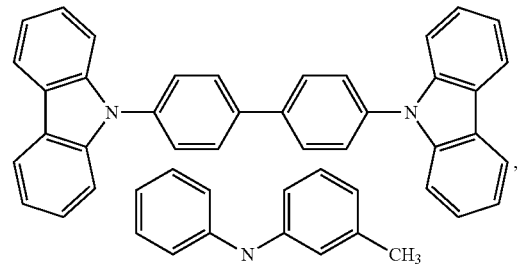,

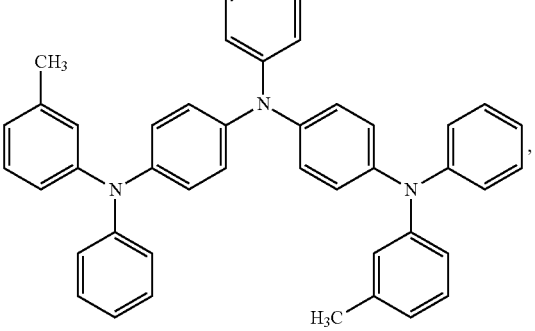,

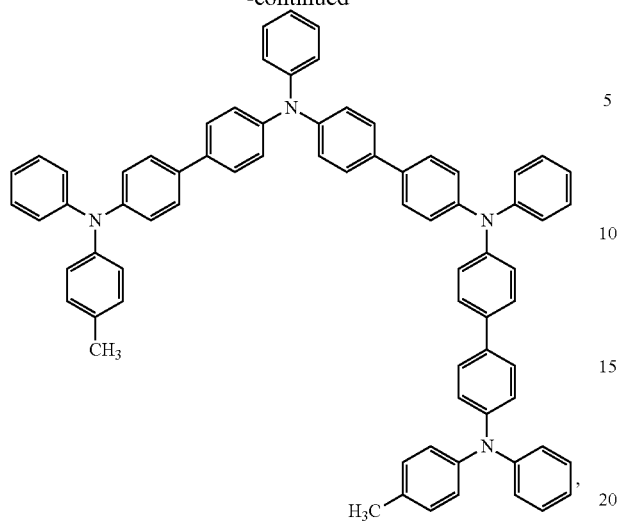

4,4',4''-tris(carbazolyl)-triphenylamine (TCTA),
(2,2',7,7'-tetrakis-(diphenylamino)-spiro-9,9'-bifluorene),
9-(10-(N-(naphthalen-1-yl)-N-phenylamino)anthracen-9-yl)-N-(naphthalen-1-yl)-N-phenylanthracen-10-amine,
9-(10-(N-biphenyl-N-2-m-tolylamino)anthracen-9-yl)-N-biphenyl-N-2-m-tolylamino-anthracen-10-amine,
9-(10-(N-phenyl-N-m-tolylamino)anthracen-9-yl)-N-phenyl-N-m-tolylanthracen-10-amine;
(iv) a low work function metal;
(v) a quinolate or substituted quinolate of a low work function metal;
(vi) lithium quinolate or lithium 2-methyl quinolate;
(vii) aluminium quinolate or a blue aluminium quinolate;
(viii) zirconium quinolate;
(ix) a compound of the formula

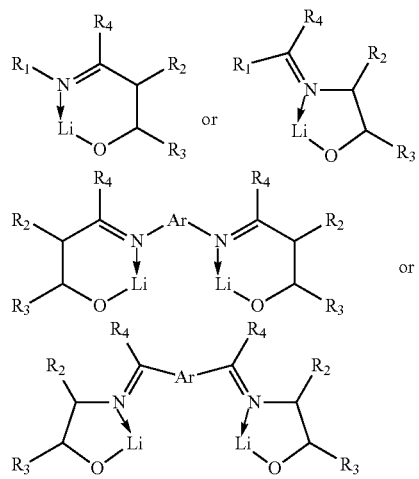

wherein
$R_1$ is a 1-5 ring aryl (including polycyclic), aralkyl or heteroaryl group which may be substituted with one or more $C_1$-$C_4$ alkyl, alkoxy or cyano;
$R_2$ and $R_3$ together form a 1-5 ring aryl (including polycyclic), aralkyl or heteroaryl group which may be substituted with $C_1$-$C_4$ alkyl, alkoxy or cyano;
$R_4$ is hydrogen, $C_1$-$C_4$ alkyl or aryl; and Ar is monocyclic, bicyclic or tricyclic aryl or heteroaryl which may be substituted with one or more $C_1$-$C_4$-alkyl or alkoxy groups,
or an oligomer thereof;
(x) a compound of formula:

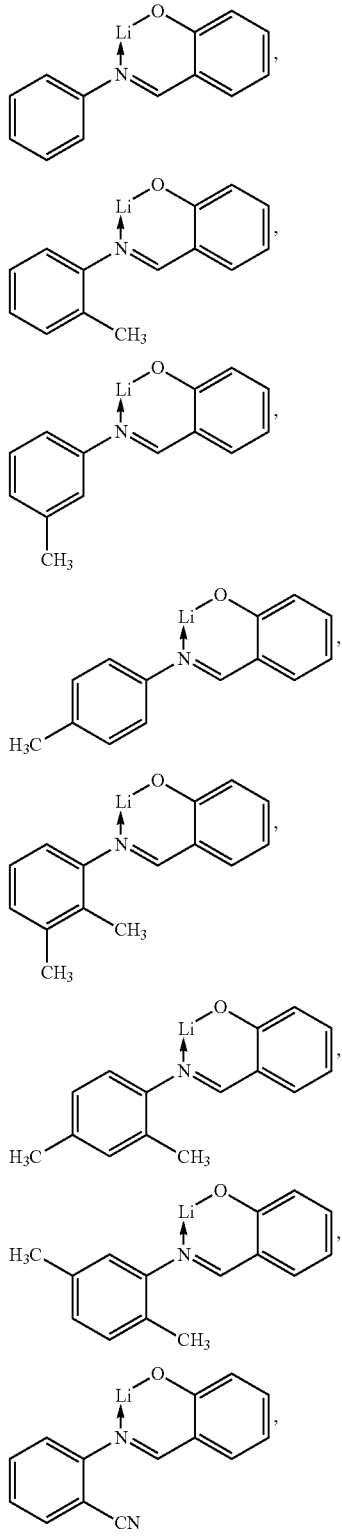

-continued

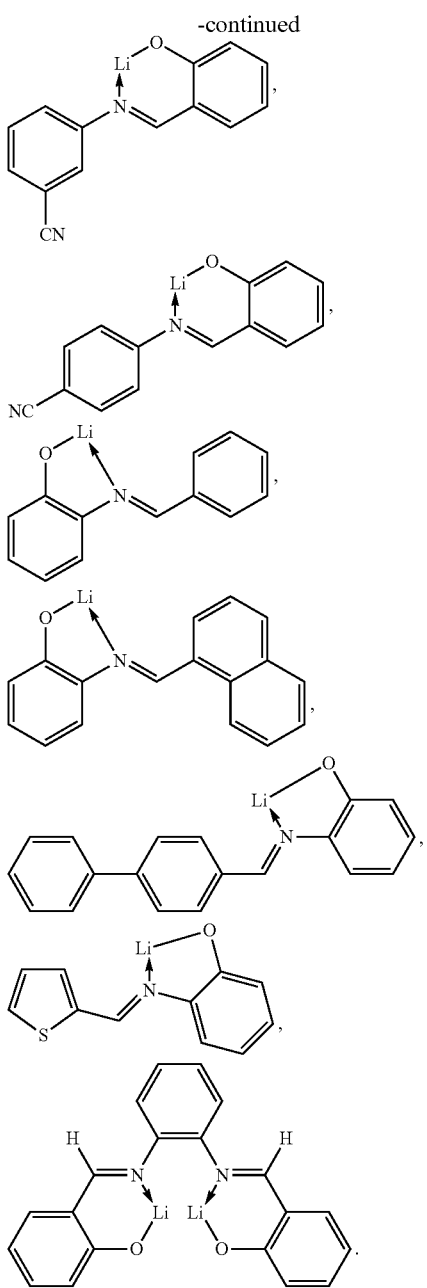

9. An optical light emitting diode device having a first electrode, a second electrode and a layer comprising the composition as claimed in claim 1 between the first and second electrodes.

10. The device of claim 9, wherein the layer is an electron transport layer.

11. The device of 9, having at least of the following features:
(i) the compound is doped with at least one fluorescent dopant;
(ii) the compound is doped with at least one phosphorescent dopant; and
(iii) the compound is doped with at lest one ion-phosphorescent dopant.

12. The device of claim 9, having at least one of the following features:
(i) an electroluminescent layer comprises a metal or metalloid complex;
(ii) an electroluminescent layer comprises as host or as luminescent material a metal quinolate, an iridium, ruthenium, osmium, rhodium, iridium, palladium or platinum complex, a boron complex or a rare earth complex;
(iii) an electroluminescent layer comprises zirconium or hafnium quinolate as host material doped with a dopant;
(iv) an electroluminescent layer comprises aluminum quinolate or a "blue" aluminum quinolate as host material doped with a dopant;
(v) an electroluminescent material comprises lithium quinolate made from a lithium alkyl or alkoxide in acetonitrile and doped with a dopant;
(vi) an electroluminescent layer comprises an aromatic tertiary amine as host material doped with a dopant;
(vii) an electroluminescent layer comprises a light-emitting conjugated polymer or copolymer or a dendrimer;
(viii) a hole injection layer is provided comprising ZnTpTP;
(viii) a hole transport layer is provided comprising α-NBP, TPD or m-MTDATA; and
(ix) the device is a flat panel display.

13. An imaging member for creation of an electrostatic latent image containing the composition as claimed in claim 1.

14. The composition according to claim 1, wherein the dopant is a n-dopant.

15. The composition according to claim 1, wherein the dopant is a n-dopant having a low work function of less than 3.7 eV.

16. The composition according to claim 1, wherein the dopant is lithium, potassium or caesium.

* * * * *